United States Patent [19]

Dreikorn et al.

[11] Patent Number: 5,411,963
[45] Date of Patent: May 2, 1995

[54] QUINAZOLINE DERIVATIVES

[75] Inventors: Barry A. Dreikorn, Lawrence; Glen P. Jourdan, Morristown; Robert G. Suhr, Greenfield, all of Ind.

[73] Assignee: DowElanco, Indianapolis, Ind.

[21] Appl. No.: 93,975

[22] Filed: Jul. 19, 1993

Related U.S. Application Data

[63] Continuation of Ser. No. 324,056, Mar. 16, 1989, abandoned, which is a continuation-in-part of Ser. No. 150,102, Jan. 29, 1988, abandoned.

[51] Int. Cl.$^6$ ............... C07D 265/00; A61K 31/505; A61K 31/62
[52] U.S. Cl. ................... 514/259; 514/260; 544/284; 544/285; 544/286; 544/287; 544/291; 544/292; 544/293
[58] Field of Search ............... 544/284–287, 544/291–293; 514/259, 260

[56] References Cited

U.S. PATENT DOCUMENTS

| | | | |
|---|---|---|---|
| 3,248,292 | 4/1966 | Minielli et al. | 167/65 |
| 4,213,987 | 7/1980 | Nakagami et al. | 544/293 |
| 4,304,778 | 12/1981 | Nakagami et al. | 544/293 |
| 4,510,307 | 4/1985 | Hidaka et al. | 544/284 |
| 4,672,116 | 6/1987 | Bandurco et al. | 544/287 |

FOREIGN PATENT DOCUMENTS

| | | |
|---|---|---|
| 0285089 | 10/1988 | European Pat. Off. |
| 322133 | 6/1989 | European Pat. Off. |
| 3028387 | 7/1980 | Germany |
| 1364307 | 8/1974 | United Kingdom |
| 1598880 | 9/1981 | United Kingdom |

OTHER PUBLICATIONS

Manhas, et al., "Chemical Abstracts", vol. 83, 1975, Col. 8515f.
Zhikhareva, et al., "Chemical Abstracts", vol. 85, 1976, Col. 85:123843q.
Hand, et al., "Chemical Abstracts", vol. 102, 1985, Col. 102:62180s.
Sayed, et al., "Chemical Abstracts", vol. 104, 1986, Col. 104:224869u.
*J. Chem. Soc. (B)* 1967, p. 892.
*J. Chem. Soc. Perkin Transactions 1,* 1975, pp. 2322–2326.
*Bull. de la Societe Chimique de France* 1963, pp. 1161–1166.
*Chemical and Pharmaceutical Bulletin 32,* p. 3690 (1984).
*Chemical and Pharmaceutical Bulletin 33,* p. 950 (1985).
*Chemie Therapeutique, vo. 2,* pp. 202–212 (1967).
Chemical Abstract 86:140078g (1977).
Chemical Abstract 84:150043q (1976).
Chemical Abstract 94:156855 (1981).
Chemical Abstract 84:105533p (1976).
Chemical Abstract 68:103651w (1968).

*Primary Examiner*—Johann Richter
*Assistant Examiner*—Catherine S. Kilby Scalzo
*Attorney, Agent, or Firm*—Donald R. Stuart

[57] ABSTRACT

Substituted quinazolines of the formula (1):

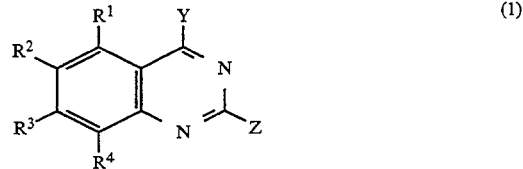

wherein:
$R^1$ to $R^4$ are independently H, halo, ($C_1$–$C_4$) alkyl, branched ($C_3$–$C_4$) alkyl, halo ($C_1$–$C_4$) alkyl, ($C_1$–$C_4$) alkoxy, $NO_2$, or $NH_2$,
provided that
at least two of $R^1$ to $R^4$ are H;
Y is H, Cl, X—W—Ar, or O—Alk;
X is O, $NR^7$, or $CR^8R^9$;
Z is H, Cl, $OCH_3$, $CH_3$, or —$NR^7$—W—Ar, provided that Z can be —$NR^7$—W—Ar only if Y is H, Cl, or $NR^7$—W—Ar and Z must be —$NR^7$—W—Ar if Y is H or Cl, which are plant fungicides, miticides, and insecticides.

61 Claims, No Drawings

QUINAZOLINE DERIVATIVES

RELATED APPLICATIONS

This application is a continuation of U.S. Ser. No. 07/324,056, filed Mar. 16, 1989, abandoned, which is a continuation-in-part of Ser. No. 07/150,102 filed Jan. 29, 1988, abandoned.

FIELD OF THE INVENTION

This invention provides new compounds that have excellent plant fungicide activity. Some of the compounds have also demonstrated insecticidal and miticidal activity. The invention also provides compositions and combination products that contain a compound of the invention as active ingredient. The invention also provides fungicidal, miticidal, and insecticidal methods.

There is an acute need for new fungicides, insecticides, and miticides, because target pathogens are rapidly developing resistance to currently used pesticides. Widespread failure of N-substituted azole fungicides to control barley mildew was observed in 1983, and has been attributed to the development of resistance. At least 50 species of fungi have developed resistance to the benzimidazole fungicides. The field performance of DMI (demethylation inhibitor) fungicides, which are now widely relied on to protect cereal crops from powdery mildew, has declined since they were introduced in the 1970's. Even recent fungicides, like the acylalanines, which initially exhibited excellent control of potato late blight and grape downy mildew in the field, have become less effective because of widespread resistance. Similarly, mites and insects are developing resistance to the miticides and insecticides in current use. Resistance to insecticides in arthropods is widespread, with at least 400 species resistant to one or more insecticides. The development of resistance to some of the older insecticides, such as DDT, the carbamates, and the organophosphates, is well known. But resistance has even developed to some of the newer pyrethroid insecticides and miticides. Therefore a need exists for new fungicides, insecticides, and miticides.

SUMMARY OF THE INVENTION

This invention provides compounds of the formula (1):

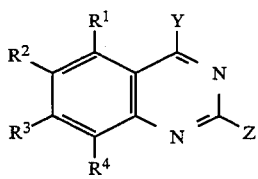

wherein:
$R^1$ to $R^4$ are independently H, halo, $(C_1-C_4)$ alkyl, branched $(C_3-C_4)$ alkyl, halo $(C_1-C_4)$ alkyl, halo $(C_1-C_4)$ alkoxy, $(C_1-C_4)$ alkoxy, halo $(C_1-C_4)$ alkylthio, OH, CN, $NO_2$, or $NH_2$, at least two of $R^1$ to $R^4$ being H;

Y is H, Cl, X—W—Ar, $CR^8R^9$-Alk, or O—Alk;

X is O, $NR^7$, or $CR^8 R^9$;

Z is H, Cl, $OCH_3$, $CH_3$, $CCl_3$, or —$NR^7$—W—Ar, provided that Z can be —$NR^7$—W—Ar only if Y is H, Cl, or —$NR^7$—W—Ar, and Z must be —$NR^7$—W—Ar if Y is H or Cl;

$R^7$ is H, $(C_1-C_4)$ alkyl, or acetyl;

$R^8$ and $R^9$ are independently H, $(C_1-C_4)$ alkyl, $(C_1-C_4)$ acyl, halo, or OH, or $R^8$ and $R^9$ combine to form a saturated or unsaturated carbocyclic ring comprising three to seven carbon atoms;

W is an alkylene chain 2 to 8 carbon atoms long, that optionally includes an O, S, SO, $SO_2$, or $NR^7$ group, and optionally includes a saturated or unsaturated carbocyclic ring comprising three to seven carbon atoms, and optionally is substituted with $(C_1-C_3)$ alkyl, $(C_2-C_4)$ alkenyl, phenyl, $(C_3-C_8)$ cycloalkyl, halo, hydroxy, or acetyl; and Ar is
  imidazolyl,
  indolyl,
  thienyl, optionally substituted with $CH_3$ or Cl,
  thiazolyl,
  1,3-benzodioxolyl,
  fluorenyl,
  cyclopentyl,
  1-methylcyclopentyl,
  cyclohexyl (hexahydrophenyl),
  cyclohexenyl (tetrahydrophenyl),
  naphthyl,
  substituted naphthyl,
  dihydronaphthyl,
  tetrahydronaphthyl,
  decahydronaphthyl,
  pyridyl,
  substituted pyridyl,
  2,3-dihydroindenyl,
or a group of the formula (2):

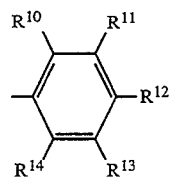

where
$R^{10}$ to $R^{14}$ are independently H, halo, I, $(C_1-C_{10})$ alkyl, branched $(C_3-C_6)$ alkyl, halo $(C_1-C_7)$ alkyl, $(C_1-C_7)$ alkoxy, halo $(C_1-C_7)$ alkoxy, phenoxy, substituted phenoxy, phenyl, substituted phenyl, phenylthio, substituted phenylthio, $NH_2$, $NO_2$, OH, acetoxy, CN, $SiR^{15}R^{16}R^{17}$, $OSiR^{15}R^{16}R^{17}$, where $R^{15}$, $R^{16}$, and $R^{17}$ are independently $C_1-C_4$ alkyl, $C_3-C_4$ branched alkyl, phenyl, or substituted phenyl, at least two of $R^{10}$ to $R^{14}$ being H;

Alk is a $(C_2-C_{18})$ saturated or unsaturated hydrocarbon chain, straight chain or branched, that optionally includes an O, S, SO, $SO_2$, or $NR^7$ group, and is optionally substituted with halo, halo $(C_1-C_4)$ alkoxy, $(C_3-C_8)$ cycloalkyl, hydroxy, or $(C_1-C_4)$ acyl;

or an acid addition salt of a compound of formula (1); provided that:
if $R^1$ to $R^4$ are all H and Y is $NR^7$—W—Ar, then Ar is naphthyl or a group of formula (2) wherein at least one of $R^{10}$ to $R^{14}$ is phenyl, substituted phenyl, phenoxy, substituted phenoxy, phenylthio, substituted phenylthio, halo $(C_1-C_4)$ alkyl, or halo $(C_1-C_4)$ alkoxy.

The final proviso excludes compounds that are known per se or that could be considered similar to known compounds.

The fungicide combinations of the invention comprise at least 1% by weight of a compound of formula (1) in combination with a second plant fungicide.

The fungicide compositions of the invention comprise a disease inhibiting and phytologically acceptable amount of compound of formula (1) in combination with a phytologically-acceptable carrier. Such compositions may optionally contain additional active ingredients, such as an additional fungicidal, miticidal, or insecticidal ingredient.

The fungicidal method of the invention comprises applying to the locus of a plant pathogen a disease inhibiting and phytologically acceptable amount of a compound of formula (1).

The insecticide and miticide combinations of the invention comprise at least 1% by weight of a compound of formula (1) in combination with a second insecticide or miticide.

The insecticide and miticide compositions of the invention comprise an insect- or mite-inactivating amount of a compound of formula (1) in combination with a carrier. Such compositions may optionally contain additional active ingredients, such as an additional fungicidal, miticidal, or insecticidal ingredient.

The insecticidal or miticidal method of the invention comprises applying to a locus of an insect- or mite-inactivating amount of a compound of formula (1), or of a combination described above.

DETAILED DESCRIPTION OF THE INVENTION

Throughout this document, all temperatures are given in degrees Celsius, and all percentages are weight percentages unless otherwise stated.

The term "halo" refers to a F, Cl, or Br atom.

The terms "$(C_1-C_3)$ alkyl", "$(C_1-C_4)$ alkyl", "$(C_2-C_{18})$ alkyl", and "$(C_1-C_{10})$ alkyl", when used alone, refer to straight chain alkyl radicals.

The terms "branched $(C_3-C_4)$ alkyl", and "branched $(C_3-C_6)$ alkyl" refer to all alkyl isomers containing the designated number of carbon atoms, excluding the straight chain isomers.

The term "$(C_1-C_7)$ alkoxy" refers to straight or branched chain alkoxy groups.

The term "halo $(C_1-C_7)$ alkyl" refers to a $(C_1-C_7)$ alkyl group, straight chain or branched, substituted with one or more halo atoms.

The term "halo $(C_1-C_7)$ alkoxy" refers to a $(C_1-C_7)$ alkoxy group substituted with one or more halo groups.

The term "halo $(C_1-C_4)$ alkylthio" refers to a $(C_1-C_4)$ alkylthio group, straight chain or branched, substituted with one or more halo atoms.

The term "substituted phenyl" refers to phenyl substituted with up to three groups selected from halo, I, $(C_1-C_{10})$ alkyl, branched $(C_3-C_6)$ alkyl, halo $(C_1-C_4)$ alkyl, hydroxy $(C_1-C_4)$ alkyl, $(C_1-C_4)$ alkoxy, halo $(C_1-C_4)$ alkoxy, phenoxy, phenyl, $NO_2$, OH, CN, $(C_1-C_4)$ alkanoyloxy, or benzyloxy.

The terms "substituted naphthyl", "substituted pyridyl" and "substituted furanyl" refer to these ring systems substituted with halo, halo $(C_1-C_4)$ alkyl, CN, $NO_2$, $(C_1-C_4)$ alkyl, $(C_3-C_4)$ branched alkyl, phenyl, $(C_1-C_4)$ alkoxy, or halo $(C_1-C_4)$ alkoxy.

The term "substituted phenoxy" refers to phenoxy substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "carbocyclic ring" refers to a saturated or unsaturated carbocyclic ring containing three to seven carbon atoms.

The term "substituted phenylthio" refers to a phenylthio group substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "unsaturated hydrocarbon chain" refers to a hydrocarbon chain containing one or two sites of unsaturation.

The term "HPLC" refers to a high-performance liquid chromatography.

COMPOUNDS

While all of the compounds of the invention are useful fungicides, certain classes are preferred for reasons of greater efficacy or ease of synthesis, viz:

1) compounds of formula (1) where at least three of $R^1$ to $R^4$ are H;
2) compounds of formula (1) where $R^4$ is F and the rest of $R^1$ to $R^4$ are H;
3) compounds of formula (1) where $R^1$ to $R^4$ are all H;
4) compounds of formula (1) where Z is H;
5) compounds of formula (1) where the alkylene chain, W, is two to four carbon atoms long.
6) compounds of formula (1) where W is $-(CH_2)_2-$;
7) compounds of formula (1) where Y is X—W—Ar;
8) compounds of preferred class 7 where Ar is a phenyl group of formula (2) wherein at least three of $R^{10}$ to $R^{14}$ are H;
9) compounds of preferred class 7 where Ar is a phenyl group of formula (2) wherein four of $R^{10}$ to $R^{14}$ are H;
10) compounds of any one of preferred classes 7 to 9 where Ar is a phenyl group of formula (2) wherein one of $R^{10}$ to $R^{14}$ is Cl, Br, $(C_1-C_4)$ alkyl, branched $(C_3-C_6)$ alkyl, halo $(C_1-C_4)$ alkyl, $(C_1-C_4)$ alkoxy, $(C_1-C_4)$ alkylthio, halo $(C_1-C_4)$ alkoxy, phenyl, substituted phenyl, phenoxy, substituted phenoxy, phenylthio, or substituted phenylthio;
11) compounds of preferred class 10 wherein $R^{10}$, $R^{11}$, $R^{13}$, and $R^{14}$ are H;
12) compounds of preferred class 10 or 11 wherein $R^{12}$ is ethoxy, propoxy, or butoxy.
13) compounds of any one of preferred classes 7 to 12 where X is O;
14) compounds of preferred class 7 where X is $NR^7$;
15) compounds of any one of preferred classes 7 to 12 where X is $NR^7$.

Compounds particularly preferred for their activity against plant pathogens are:

4-[2-(4-phenoxyphenyl)ethoxy]quinazoline,
4-[2-[4-(tetrafluoroethoxy)phenyl]ethoxy]quinazoline,
4-[2-[4-(trifluoromethoxy)phenyl]ethoxy]quinazoline,
4-[2-(4-ethoxyphenyl)ethoxy]quinazoline,
4-[2-(4-methoxyphenyl)ethoxy]quinazoline,
4-[2-(4-propoxyphenyl)ethoxy]quinazoline,
4-[2-[4-(thioethyl)phenyl]ethoxy]quinazoline,
4-[2-[4-(t-butyl)phenyl]ethoxy]quinazoline,
4-[2-(4-chlorophenyl)ethoxy]quinazoline,
4-[2-(4-chlorophenyl)ethoxy]-8-fluoroquinazoline, 4-[2-(2-naphthyl)ethoxy]quinazoline,
4-[2-(1,1′-biphenyl)-4-ylethoxy]quinazoline,
4-[2-(4-methylphenyl)ethoxy]quinazoline,
8-fluoro-N-[2-(2-naphthyl)ethyl-4-quinazolinamine,
N-[2-(3-phenoxyphenyl)ethyl]-4-quinazolinamine,
N-[2-[2-(trifluoromethyl)phenyl]ethyl]-4-quinazolinamine,
N-[2-[3-(trifluoromethyl)phenyl]ethyl]-8-fluoro-4-quinazolinamine,
N-[2-[4-(trifluoromethyl)phenyl]ethyl]-4-quinazolinamine,
N-[2-(2-naphthyl)ethyl]-4-quinazolinamine,
8-fluoro-N-[2-(4-chlorophenyl)ethyl]-4-quinazolinamine,
8-fluoro-N-[2-[4-(i-propyl)phenyl]ethyl]-4-quinazolinamine,
N,N′-bis(1-methyl-2-phenylethyl)-2,4-quinazolinediamine, and
N,N′-bis(2-phenylpropyl)-2,4-quinazolinediamine.

Particularly preferred for their activity against mites and insects are compounds of formula (1) wherein Y is X—W—Ar, Z is H, and Ar is a substituted phenyl group of formula (2) wherein $R^{12}$ is Cl, Br, ($C_1$-$C_4$) alkyl, branched ($C_3$-$C_4$) alkyl, phenyl, substituted phenyl, phenoxy, or substituted phenoxy. Examples include:

4-[2-[4-(t-butyl)phenyl]ethoxy]quinazoline,
4-[2-(4-chlorophenyl)ethoxy]quinazoline,
4-[2-(1,1′-biphenyl)-4-ylethoxy]quinazoline,
4-[2-(4-methylphenyl)ethoxy]quinazoline,
4-[2-[4-(i-propyl)phenyl]ethoxy]quinazoline,
8-fluoro-4-[2-(1,1′-biphenyl)-4-ylethoxy]quinazoline,
8-fluoro-4-[2-[4-(t-butyl)phenyl]ethoxy]quinazoline,
8-fluoro-N-[2-[4-(t-butyl)phenyl]ethyl]-4-quinazolinamine,
8-fluoro-N-[2-(4-phenoxyphenyl)ethyl]-4-quinazolinamine,
8-fluoro-N-[2-(1,1′-biphenyl)-4-ylethyl]-4-quinazolinamine,
N-[2-(1,1′-biphenyl)-4-ylethyl]-N-(4-quinazolinyl)acetamide, and
N-[2-(1,1′-biphenyl)-4-ylethyl]-4-quinazolinamine.

SYNTHESIS

The compounds of this invention are made using well known chemical procedures. The required starting materials are commercially available, or they are readily synthesized using standard procedures.

Synthesis of Compounds Wherein Y is O—Alk or O—W—Ar

The compounds of formula (1) wherein Y is O—Alk or O—W—Ar were made by condensing a compound of formula (3):

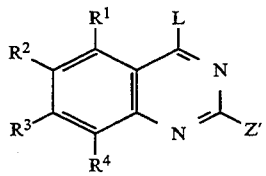

(3)

where $R^1$ to $R^4$ are as previously defined, L is Cl or 1,2,4-triazol-1-yl, and Z′ is H, Cl, $CH_3$, $OCH_3$, or $CCl_3$ with an alcohol of the formula (4a) or (4b):

HO—Alk (4a)

HO—W—Ar (4b)

where
Alk, W, and Ar are as previously defined.

The reaction is preferably carried out in the presence of a strong base, such as sodium hydride, in a non-reactive organic solvent, such as DMF, at a temperature in the range of 0° to 25° C.

Synthesis of Compounds Wherein Y is $NR^7$—W—Ar

The compounds of formula (1) wherein Y is $NR^7$—W—Ar were prepared by condensing a compound of formula (3) with an amine of the formula (5)

(5)

where
$R^{7′}$ is H or ($C_1$-$C_4$) alkyl, and
Ar is as previously defined.

The chloride of formula (3) is allowed to react with an appropriate amine at a wide variety of temperatures (20°-180° C.), preferably in the presence of an acid acceptor, such as triethylamine. The reaction may be carried out neat, or in a non-reactive organic solvent. Compounds where $R^7$ is acetyl were prepared from amines where $R^7$ is H, which were allowed to react with an acylating agent such as an acetyl chloride or acetic anhydride. In cases where the starting material of formula (3) is one wherein Z′ is Cl, a mixture of products is obtained which are separable using liquid chromatography.

Synthesis of Compounds Wherein Y is $CR^8R^9$—Alk or $CR^8R^9$—W—Ar

The compounds of formula (1) wherein Y is $CR^8R^9$—Alk or $CR^8R^9$—W—Ar can be made using the process described in the *J. Heterocyclic Chemistry*, Vol. 14, 1082–1083 (1977)—authors A. Scoville and F. X. Smith.

This procedure involves hydrolysis and decarboxylation of 5-substituted-5-(4-quinazolyl)-barbituric acids of the formula (6) or (7)

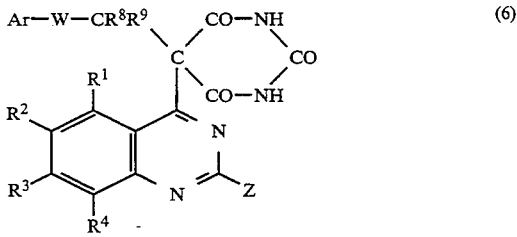

(6)

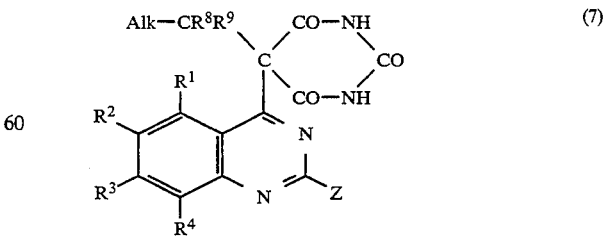

(7)

wherein $R^1$, $R^2$, $R^3$, $R^4$, $R^8$, $R^9$, Z′, W, Alk, and Ar are as previously defined. The 5-substituted-5-(4-quinazolyl)barbituric acid of formula (6) or (7) is dissolved in a solution of sodium hydroxide and water and refluxed. The solution is then made slightly acidic and again refluxed.

Some compounds of formula (1) wherein Y is $CR^8R^9$—Alk or $CR^8R^9$—W—Ar were prepared by reacting a compound of formula (3) where L is H with a Grignard reagent of the formula Y'—MgX or a lithio reagent of the formula Y'Li, where Y' is $CR^8R^9$—Alk or $CR^8R^9$—W—Ar, and X is halo, to provide a 3,4-dihydroquinazoline, which was then oxidized to provide a compound of the invention. Typical reaction conditions were those described in Armarego and Smith, *J. Chem. Soc.*, page 5360 (1965).

The acid addition salts of compounds of formula (1) are obtained in the usual way.

Compounds of formula (1) wherein Z is $OCH_3$ can be obtained by treating a compound of formula (1) wherein Z is Cl with sodium methoxide.

Accordingly, the invention also provides a process for preparing a compound of formula (1) which comprises (a) condensing a compound of formula (3)

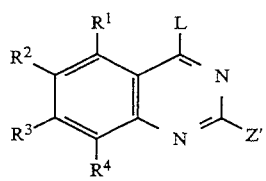
(3)

wherein $R^1$ to $R^4$ are as previously defined, L is Cl, or 1,2,4-triazol-1-yl, and Z' is H, Cl, $CH_3$, or $OCH_3$, with an alcohol of the formula (4a) or (4b)

HO—Alk (4a)

HO—W—Ar (4b)

wherein W and Ar are as previously defined to produce a compound of formula (1) wherein Y is O—Alk or O—W—Ar; or (b) condensing a compound of formula (3) as defined above with an amine of the formula (5)

(5)

where $R^{7'}$ is H or $(C_1-C_4)$ alkyl, and Ar is as previously defined, to provide a compound of formula (1) where Y is $NR^{7'}$—W—Ar; or (c) acylating a compound of formula (1) wherein Y is —NH—W—Ar to provide a compound of formula (1) wherein Y is $NR^7$—W—Ar and $R^7$ is acetyl; or (d) hydrolyzing and decarboxylating a 5-substituted-5-(4-quinazolyl)barbituric acid of the formula (6) or (7)

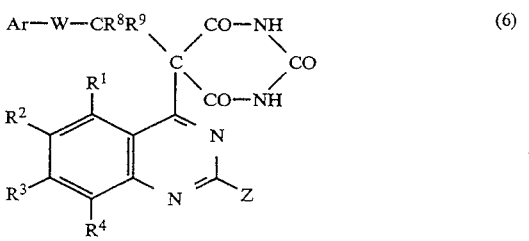
(6)

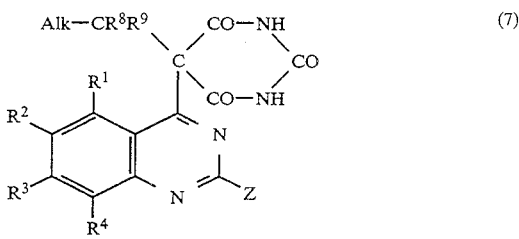
(7)

wherein $R^1$, $R^2$, $R^3$, $R^4$, $R^8$, $R^9$, Z', W, Alk, and Ar are as previously defined, to produce a compound of formula (1) wherein Y is $CR^8R^9$—Alk or $CR^8R^9$—W—Ar.

Preparation of Quinazoline Starting Materials

Quinazoline starting materials are commercially available or readily prepared using conventional procedures. For example, 4-hydroxy quinazolines can be prepared from commercially available anthranilic acids via condensation with excess formamide at reflux (M. Endicott et al. *J. Am. Chem. Soc.*, 1946, 68, 1299). Alternatively hydroxy quinazolines can be prepared in dioxane at reflux using Gold's reagent (J. Gipton; Correia, K.; Hertel, G. *Synthetic Communications*, 1984, 14, 1013). Once in hand, the 4-hydroxy quinazoline is chlorinated under standard conditions to provide 4-chloroquinazoline starting materials.

Intermediates of formula (3) wherein L is 1,2,4-triazol-1-yl, can be prepared, for example, by adding $POCl_3$ dropwise to a mixture of a 4-hydroxyquinazoline (1 equiv.) of formula (9) and 1,2,4-triazole (3 equiv.) in pyridine at room temperature.

In a preferred procedure, a 4-chloroquinazoline of formula (3) is prepared, and then converted to the desired product of formula (1) without isolation. If phosphorous halide compounds, such as $PCl_5$ and $POCl_3$ are used to prepare the 4-chloroquinazoline of formula (3), a large excess of phosphorous halide is required. The 4-chloroquinazoline must then be isolated before it can be used to prepare compounds of formula (1), because the excess phosphorous halide would otherwise react with the alcohol of formula (4) or amine of formula (5). It is undesirable to isolate the 4-chloroquinazoline, because it is unstable. It is also mutagenic and smells bad. To avoid these difficulties, the 4-chloroquinazoline can be prepared from the corresponding 4-hydroxyquinazoline using a triphenylphosphite-halogen complex of the formula (8)

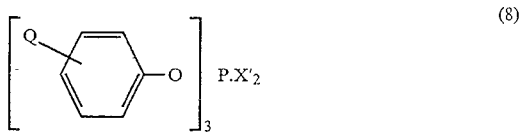
(8)

where Q is H, halo, $(C_1-C_4)$ alkyl, or $(C_1-C_4)$ alkoxy and X' is Cl or Br as the halogenating reagent. These halogenating reagents are described in U.S. Pat. No. 4,230,644, where their use in converting alcohols to alkyl halides and amides to imino chlorides is described. The prior art did not suggest use of these halogenating reagents to halogenate nitrogen heterocycles.

The triphenylphosphite-halogen reagent of formula (8) is prepared by reacting chlorine or bromine with a suitable triphenylphosphite in a substantially anhydrous inert organic solvent, such as a hydrocarbon, or halogenated hydrocarbon, at a temperature below 30° C., preferably −15° C. to 0° C. The triphenylphosphite-halogen reagent is unstable and converts on standing to a less reactive "thermodynamic" form. The "kinetic" form can be stabilized in solution by adding up to 1 mole of a tertiary amine base, such as pyridine, to the reaction mixture, and by operating at lower temperatures, e.g. less than about −15° C.

To minimize the opportunity for equilibration to the less reactive thermodynamic product, the halogenating reagents may be prepared immediately before they are utilized, or preferably are prepared in the presence of the 4-hydroxy substrate so that reaction is immediate. Typically, the halogen is added to a mixture of the triphenylphosphite, pyridine and 4-hydroxyquinazoline in a suitable solvent.

Preferably, 1 to 1.3 equivalents of halogenating reagent of formula (8) are used per equivalent of 4-hydroxy-quinazoline. Following preparation of the 4-chloroquinazoline hydrochloride intermediate, excess halogenating reagent may be quenched by adding a small amount of water to the reaction mixture. The alcohol of formula (4) or amine of formula (5) may then be reacted with the 4-chloroquinazoline intermediate without isolation.

Accordingly, compounds of formula (1) wherein Y is O—Alk, O—W—Ar, or $NR^{7'}$—W—Ar, can be made by (a) reacting a 4-hydroxyquinazoline of formula (9)

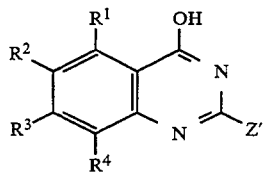

(9)

wherein $R^1$, $R^2$, $R^3$, $R^4$, and Z′ are as defined above, with 1 to 1.3 equivalents of a halogenating reagent of the formula (8)

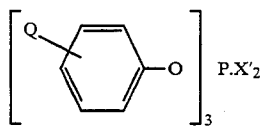

(8)

wherein Q is H, halo, $(C_1-C_4)$ alkyl, or $(C_1-C_4)$ alkoxy and X′ is Cl or Br, in an inert organic solvent at a temperature below 30° C., and (b) without isolation of the 4-chloroquinazoline produced in step (a), reacting it with an alcohol of the formula (4a) or (4b)

HO—Alk    (4a), or

HO—W—Ar    (4b), where Alk, W, and Ar are as previously defined, or with an amine of the formula (5)

$HNR^{7'}$—W—Ar    (5)

where $R^{7'}$, W, and Ar are as previously defined.

EXAMPLES 1–203

The following examples are compounds actually prepared by the above described general procedures. The melting point is given for each compound. In addition, although the data has not been included, each compound was fully characterized by NMR, IR, mass spectra, and combustion analysis. Specific illustrative preparations for the compounds of Examples 2, 5, 29, 53, 74, 85, and 96 follow the tabular listing.

| EXAMPLE NUMBER | COMPOUND | M.P. |
|---|---|---|
| 1 | N,N′-bis(2-phenylethyl)-2,4-quinazoline-diamine | oil |
| 2 | 4-[2-[4-(t-butyl)phenyl]ethoxy]quinazoline | 70–71° C. |
| 3 | 4-(decyloxy)quinazoline | oil |
| 4 | N-[2-(5-chloro-2-thienyl)ethyl]-2-phenyl-4-quinazolinamine | 114–116° C. |
| 5 | 4-[2-(4-chlorophenyl)ethoxy]quinazoline | 57–58° C. |
| 6 | N-(2-cyclohexyl-2-phenylethyl)-N-4-quinazolinylacetamide | oil |
| 7 | N,N′-bis[2-[4-(i-propyl)phenyl]ethyl]-2,4-quinazolinediamine | 224–226° C. |
| 8 | N-4-quinazolinyl-N-[2-[2-(trifluoromethyl)phenyl]ethyl]acetamide | oil |
| 9 | N-[2-(1,3-benzodioxol-5-yl)ethyl]-N-4-quinazolinylacetamide | 93–95° C. |
| 10 | 8-fluoro-4-[2-(4-phenoxyphenyl)ethoxy]-quinazoline | 100–102° C. |
| 11 | 4-[2-(2-chlorophenyl)ethoxy]quinazoline | 67–69° C. |
| 12 | 4-(dodecyloxy)quinazoline | 30–32° C. |
| 13 | 4-[2-(3-methoxyphenyl)ethoxy]quinazoline | oil |
| 14 | 4-[2-(2-methoxyphenyl)ethoxy]quinazoline | 124–125° C. |
| 15 | 4-[2-(4-ethoxyphenyl)ethoxy]quinazoline | 80–81° C. |
| 16 | 8-fluoro-4-[2-[4-(i-propyl)phenyl]-ethoxyl-quinazoline | 53–55° C. |
| 17 | N-[2-(4-chlorophenyl)propyl]-8-fluoro-4-quinazolinamine | 151–153° C. |
| 18 | 4-(1-methyl-2-phenylethoxy)quinazoline | oil |
| 19 | 4-hydroxy-α-[(4-quinazolinylamino)-methyl]benzenemethanol | 203–205° C. |
| 20 | 4-[2-(9H-fluoren-2-yl)ethoxy]quinazoline | 135–137° C. |
| 21 | 4-[2-(4-ethoxy-3-methoxyphenyl)ethoxy]-quinazoline | 62–63° C. |
| 22 | 4-[2-(4-bromophenyl)ethoxy]quinazoline | 64–65° C. |
| 23 | N-[2-(1-naphthyl)ethyl]-4-quinazolinamine | 187–189° C. |
| 24 | N,N′-bis(3-phenylpropyl)-2,4-quinazoline-diamine | oil |
| 25 | N,N′-bis[2-(2-methoxyphenyl)ethyl]-2,4-quinazolinediamine | thick oil |
| 26 | N,N′-bis(1-methyl-2-phenylethyl)-2,4-quinazolinediamine | very thick oil |
| 27 | N,N′-bis(2-phenylpropyl)-2,4-quinazoline-diamine | very thick oil |
| 28 | N,N′-bis[2-(4-methylphenyl)ethyl]-2,4-quinazolinediamine | 110–111° C. |
| 29 | 4-(3-phenylpropyl)quinazoline | oil |
| 30 | N-(4-quinazolinyl)-N-[2-[3-(trifluoromethyl)phenyl]ethyl]acetamide | oil |
| 31 | 8-fluoro-N-[2-(2-naphthyl)ethyl]-4-quinazolinamine | 187–188° C. |
| 32 | N,N′-bis[2-(2-naphthyl)ethyl]-2,4-quinazolinediamine | 264–266° C. |
| 33 | 4-(2-phenylethoxy)quinazoline | 47–48° C. |
| 34 | 2-methoxy-N-[2-[3-(trifluoromethyl)-phenyl]ethyl]-4-quinazolinamine | 124–125° C. |
| 35 | 2-methyl-N-[2-(4-chlorophenyl)ethyl]-4-quinazolinamine | 165–176° C. |
| 36 | N-[2-(4-chlorophenyl)ethyl]-5-methyl-4-quinazolinamine | oil |
| 37 | N-[2-(4-chlorophenyl)ethyl]-6-bromo-4-quinazolinamine | 203–206° C. |
| 38 | N-[2-(3-phenoxyphenyl)ethyl]-4-quinazolinamine | 137–139° C. |
| 39 | N-[2-[2-(trifluoromethyl)phenyl]ethyl]- | 151–153° C. |

| EXAMPLE NUMBER | COMPOUND | M.P. |
|---|---|---|
| 40 | 7-chloro-N-[2-[4-(i-propyl)phenyl]ethyl]-4-quinazolinamine | 157–159° C. |
| 41 | 4-[2-(3-chlorophenyl)ethoxy]quinazoline | 100° C. |
| 42 | 4-(phenylbutoxy)quinazoline | 40° C. |
| 43 | 4-[2-(2,4,6-trimethylphenyl)ethoxy]quinazoline | 90° C. |
| 44 | 6-(trifluoromethoxy)-N-[2-(4-phenoxyphenyl)ethyl]-4-quinazolinamine | 112–114° C. |
| 45 | N-[2-(2-phenoxyphenyl)ethyl]-4-quinazolinamine | 148–150° C. |
| 46 | N-(2-cyclohexylethyl)-8-fluoro-4-quinazolinamine | 167–169° C. |
| 47 | 4-[2-[2-(trifluoromethyl)phenyl]ethoxy]quinazoline | 115° C. |
| 48 | 4-[2-(2-fluorophenyl)ethoxy]quinazoline | 52° C. |
| 49 | 4-[2-(4-methoxyphenyl)ethoxy]quinazoline | 47° C. |
| 50 | N-[2-[3-(trifluoromethyl)phenyl]ethyl]-8-fluoro-4-quinazolinamine | 151–153° C. |
| 51 | 4-[2-[3-(trifluoromethyl)phenyl]ethoxy]quinazoline | oil |
| 52 | N-[2-[4-(trifluoromethyl)phenyl]ethyl]-4-quinazolinamine | 162–163° C. |
| 53 | N-[2-(2-naphthyl)ethyl]-4-quinazolinamine | 172–174° C. |
| 54 | 4-[2-(2-thienyl)ethoxy]quinazoline | 62–63° C. |
| 55 | 4-[2-(4-chlorophenyl)ethoxy]-8-fluoroquinazoline | 85–87° C. |
| 56 | 8-fluoro-4-[2-[2-(trifluoromethyl)phenyl]ethoxy]quinazoline | 78–81° C. |
| 57 | 6-chloro-N-[2-(2-phenoxyphenyl)ethyl]-4-quinazolinamine | 175–177° C. |
| 58 | N-[2-(1-cyclohexen-1-yl)ethyl]-8-fluoro-4-quinazolinamine | 120° C. |
| 59 | 2-ethoxy-4-[2-(4-quinazolinylamino)ethyl]phenol | 133–135° C. |
| 60 | 4-(2-phenylpropoxy)quinazoline | oil |
| 61 | N-(2,2-diphenylethyl)-8-fluoro-4-quinazolinamine | 179–181° C. |
| 62 | 4-(decyloxy)-8-fluoroquinoline | 52–53° C. |
| 63 | N-[3-(1,1'-biphenyl)-4-ylpropyl]-4-quinazolinamine | 127–130° C. |
| 64 | 7-chloro-N-[3-(1,1'-biphenyl)-4-ylpropyl]-4-quinazolinamine | 153–155° C. |
| 65 | 4-[2-(4-ethylphenyl)ethoxy]quinazoline | oil |
| 66 | 8-fluoro-4-[2-(2-naphthyl)ethoxy]quinazoline | 100–102° C. |
| 67 | 4-(2,2-diphenylethoxy)quinazoline | 77–78° C. |
| 68 | 4-[2-(3-phenoxyphenyl)ethoxy]quinazoline | oil |
| 69 | 4-[2-(4-phenoxyphenyl)ethoxy]quinazoline | oil |
| 70 | 4-(2-cyclohexylethoxy)-8-fluoroquinazoline | 81–83° C. |
| 71 | N-[2-(1,1'-biphenyl)-3-ylethyl]-4-quinazolinamine | 152–154° C. |
| 72 | [3-(3-methoxyphenyl)propyl]quinazoline | oil |
| 73 | 4-[2-(3,4-dimethoxyphenyl)ethoxy]quinazoline | 92–93° C. |
| 74 | N,N'-bis[2-(2-thienyl)ethyl]-2,4-quinazolinediamine | oil |
| 75 | 7-chloro-N-[2-(2-thienyl)ethyl]-4-quinazolinamine | 162–163° C. |
| 76 | 8-fluoro-N-[2-(4-trifluoromethylphenyl)ethyl]-4-quinazolinamine | 191–193° C. |
| 77 | 8-fluoro-N-[2-(4-methylphenyl)ethyl]-4-quinazolinamine | 228–229° C. |
| 78 | 8-fluoro-N-[2-(4-chlorophenyl)ethyl]-4-quinazolinamine | 197–200° C. |
| 79 | 6-bromo-N-[2-[4-(i-propyl)phenyl]ethyl]-4-quinazolinamine | 158–161° C. |
| 80 | 4-[2-(2-naphthyl)ethoxy]quinazoline | 84° C. |
| 81 | N-[2-(2-naphthyl)ethyl]-N-4-quinazolinylacetamide | oil |
| 82 | N-[2-(1-cyclohexen-1-yl)ethyl]-4-quinazolinamine | 129–131° C. |
| 83 | N-4-quinazolinyl-N-[2-(4-(trifluoromethyl)phenyl]ethyl]acetamide | 81–84° C. |
| 84 | 4-[2-(4-fluorophenyl)ethoxy]quinazoline | 93–94° C. |
| 85 | 4-[2-(1,1'-biphenyl)-4-ylethoxy]quinazoline | 72–74° C. |
| 86 | N-[2-[3-(trifluoromethyl)phenyl]ethyl]-4-quinazolinamine | 123–125° C. |
| 87 | 4-[2-(4-methylphenyl)ethoxy]quinazoline | 70–71° C. |
| 88 | 4-[2-[4-(i-propyl)phenyl]ethyl]quinazoline | 45° C. |
| 89 | 8-fluoro-N-(2-phenylethyl)-4-quinazolinamine | 195–197° C. |
| 90 | 6-chloro-N-[2-(1,1'-biphenyl)-4-ylethyl]-4-quinazolinamine | 160–162° C. |
| 91 | 4-[2-(1-naphthyl)ethoxy]quinazoline | 85° C. |
| 92 | N-(1-methyl-3-phenylpropyl)-4-quinazolinamine | 130–132° C. |
| 93 | 8-fluoro-4-[2-(1,1'-biphenyl)-4-ylethoxy]quinazoline | 120–122° C. |
| 94 | 8-fluoro-4-[2-[4-(t-butyl)phenyl]ethoxy]quinazoline | 92–94° C. |
| 95 | 8-fluoro-4-(2-phenylethoxy)quinazoline | 57–59° C. |
| 96 | 8-fluoro-N-[2-[4-(i-propyl)phenyl]ethyl]-4-quinazolinamine | 170–172° C. |
| 97 | 4-[2-(3-methylphenyl)ethoxy]quinazoline | 36° C. |
| 98 | N-[2-(4-aminophenyl)ethyl]-4-quinazolinamine | 164–166° C. |
| 99 | 8-fluoro-4-[2-(4-methylphenyl)ethoxy]quinazoline | 72–74° C. |
| 100 | 8-fluoro-N-[2-[4-(t-butyl)phenyl]ethyl]-4-quinazolinamine | 205–207° C. |
| 101 | 8-fluoro-N-[2-(4-phenoxyphenyl)ethyl]-4-quinazolinamine | 134–136° C. |
| 102 | 8-fluoro-N-[2-(1,1'-biphenyl)-4-ylethyl]-4-quinazolinamine | 194–196° C. |
| 103 | 4-[2-(2-methylphenyl)ethoxy]quinazoline | 85° C. |
| 104 | N-[2-(4-phenoxyphenyl)ethyl]-4-quinazolinamine | 126–128° C. |
| 105 | α-[(4-quinazolinylamino)methyl]-2-naphthalenemethanol | 220–223° C. |
| 106 | N-[2-(1,1'-biphenyl)-4-ylethyl]-4-quinazolinamine | 175–177° C. |
| 107 | N-[2-[3-(trifluoromethyl)phenyl]ethyl]-2-chloro-4-quinazolinamine | 171–173° C. |
| 108 | N-[2-(1,1'-biphenyl)-4-ylethyl]-N-(4-quinazolinyl)acetamide | oil |
| 109 | N-[2-[4-(i-propyl)phenyl]ethyl]-N-4-quinazolinylacetamide | 110–112° C. |
| 110 | 4-[2-(2-chlorophenoxy)ethoxy]quinazoline | 179–180° C. |
| 111 | 4-[2-(3-hydroxyphenyl)ethoxy]quinazoline | 135–137° C. |
| 112 | 8-fluoro-4-[2-(3,4-dimethoxyphenyl)ethoxy]quinazoline | 80–82° C. |
| 113 | 8-fluoro-4-[2-[4-(2-methylpropyl)phenyl]propoxy]quinazoline | 90–92° C. |
| 114 | 4-[2-(2-hydroxyphenyl)ethoxy]quinazoline | 166–168° C. |
| 115 | 4-[2-(4-hydroxyphenyl)ethoxy]quinazoline | 204–206° C. |
| 116 | 8-fluoro-4-[2-(1,1'-biphenyl)-4-ylethoxy]quinazoline | oil |
| 117 | 4-[3-(4-chlorophenyl)propyl]quinazoline | oil |
| 118 | 8-fluoro-4-[2-(4-trifluoromethyl)ethoxy]quinazoline | 90–93° C. |
| 119 | 8-fluoro-4-[3-(4-phenoxyphenyl)propoxy]quinazoline | NA |
| 120 | 4-[2-(3-acetoxyphenyl)ethoxy]quinazoline | oil |
| 121 | 4-[3-(4-hydroxyphenyl)propoxy]quinazoline | 157–159° C. |
| 122 | 4-(2,2-dimethylbutoxy)quinazoline | oil |
| 123 | N-benzyl-N-methyl-N-[3-(quinazolin-4-yloxy)propyl]amine | oil |
| 124 | 4-[2-[2-[dimethyl-(1,1-dimethylethyl)silyloxy]phenyl]ethoxy]quinazoline | oil |
| 125 | 8-fluoro-4-[3-[4-ethoxyphenyl]propoxy]quinazoline | 73–75° C. |
| 126 | 4-[3-[4-(1-methylethyl)phenyl]propyl]quinazoline | 67–68° C. |
| 127 | 4-[3-[4-(1,1-dimethylethyl)phenyl]propyl]quinazoline | 47–48° C. |
| 128 | 4-[2-[3,5-di(trifluoromethyl)phenyl]ethoxy]quinazoline | 65–67° C. |
| 129 | 4-[(3-methoxy)butoxyquinazoline | oil |
| 130 | 4-[3-ethenyl-5-phenyl-pentyloxy]quinazoline | oil |

-continued

| EXAMPLE NUMBER | COMPOUND | M.P. |
|---|---|---|
| 131 | 8-fluoro-4-[2-(2-methoxyphenyl)ethoxy]-quinazoline | 80–82° C. |
| 132 | 8-fluoro-4-[2-(4-methoxyphenyl)ethoxy]-quinazoline | 78–80° C. |
| 133 | 8-fluoro-4-[2-3-(trifluoromethyl)phenyl]-ethoxy]quinazoline | 72–74° C. |
| 134 | 4-[2-[4-(trifluoromethyl)phenyl]ethoxy]-quinazoline | oil |
| 135 | 4-[2-[2-(1-methylethyl)phenyl]ethoxy]-quinazoline | oil |
| 136 | 7-chloro-4-[2-[4-(1,1-dimethylethyl)-phenyl]ethoxy]quinazoline | 128–130° C. |
| 137 | 4-[2-[3-(phenylthio)phenyl]ethoxy]-quinazoline | 65–69° C. |
| 138 | 4-[3-[4-(1,1-dimethylethyl)phenyl]propoxy]-quinazoline | oil |
| 139 | 8-methyl-4-[2-[4-(1,1-dimethylethyl)-phenyl]ethoxy]quinazoline | oil |
| 140 | 6-chloro-N-[3-[4-(1,1-dimethylethyl)-phenyl]propyl]-4-quinazoline | 100–101° C. |
| 141 | 8-fluoro-4-[2-(1-naphthyl)ethoxy]-quinazoline | 114° C. |
| 142 | 4-[2-(1,1'-biphenyl)-4-ylbutoxy]-quinazoline | oil |
| 143 | 4-[3-[4-(1-methylethyl)phenyl]propoxy]-quinazoline | oil |
| 144 | 4-[2-(4'-fluoro-1,1'-biphenyl)-4-yl-ethoxy]quinazoline | 92–94° C. |
| 145 | 4-[2-[2,6-bis(trifluoromethyl)phenyl]-ethoxy]quinazoline | 44–45° C. |
| 146 | 4-[2-[3-(1-methylethoxy)phenyl]ethoxy]-quinazoline | oil |
| 147 | 4-[2-[4-hydroxy-3-methoxyphenyl]ethoxy]-quinazoline | 68–70° C. |
| 148 | 4-[(1-benzyl-3-buten-2-yl)oxy]quinazoline | oil |
| 149 | 8-fluoro-4-[3-[4-(1,1-dimethylethyl)-phenyl]propoxy]quinazoline | NA |
| 150 | 4-[3,5,5-trimethylhexyloxy]quinazoline | oil |
| 151 | 4-[3-(4-phenoxyphenyl)propoxy]quinazoline | oil |
| 152 | 8-fluoro-4-[3-[4-(1-methylethyl)phenyl]-propoxy]quinazoline | oil |
| 153 | 4-[2-[4-[dimethyl-(t-butyl)silyloxy]-phenyl]ethoxy]quinazoline | oil |
| 154 | 4-[3-(4-methoxyphenyl)propyl]quinazoline | 71–72° C. |
| 155 | 4-[3-(4-ethoxyphenyl)propyl]quinazoline | 48–49° C. |
| 156 | 8-fluoro-4-[2-(4-butoxyphenyl)ethoxy]-quinazoline | 59–61° C. |
| 157 | N-[2-(2-trifluoromethylphenyl)ethyl]-8-fluoro-4-quinazolinamine | 179–181° C. |
| 158 | 4-[3-(4-ethoxyphenyl)propoxy]quinazoline | 44–45° C. |
| 159 | 8-fluoro-4-[2-(2,4-difluorophenyl)-ethoxy]quinazoline | 102–104° C. |
| 160 | N-[2-(4-benzyloxyphenyl)ethyl]-8-methyl-4-quinazolinamine | 133–135° C. |
| 161 | 4-[2-(4-phenoxyphenyl)propoxy]quinazoline | NA |
| 162 | 4-[2-[4-(2-fluorophenoxy)phenyl]ethoxy]-quinazoline | oil |
| 163 | 8-fluoro-4-[2-(3-phenoxyphenyl)ethoxy]-quinazoline | 58–60° C. |
| 164 | 4-[3-(4-phenoxyphenyl)propyl]quinazoline | 94–95° C. |
| 165 | 4-(3-methyl-2-phenylbutoxy)quinazoline | oil |
| 166 | 8-chloro-N-[2-(3-phenoxyphenyl)ethyl]-4-quinazolinamine | 177–179° C. |
| 167 | 4-[2-[4-(2-methylpropyl)phenyl]propoxy]-quinazoline | 57–59° C. |
| 168 | 4-[4-[4-(i-propyl)phenyl]butoxy]-quinazoline | oil |
| 169 | N-ethyl-N-[2-(4-quinazolinyloxy)ethyl]-benzenamine | 82–83° C. |
| 170 | 4-[2-(4-ethoxyphenyl)ethoxy]-8-fluoro-quinazoline | 75–76° C. |
| 171 | 7-chloro-N-[2-(3-phenoxyphenyl)ethyl]-4-quinazolinamine | 122–124° C. |
| 172 | 2-(trichloromethyl)-4-[2-[4-(t-butyl)-phenyl]ethoxy]quinazoline | 105–107° C. |
| 173 | 4-[2-(1,1'-biphenyl)-3-ylethoxy]-quinazoline | oil |
| 174 | 6-chloro-4-[2-[4-(t-butyl)phenyl]ethoxy]-quinazoline | 91–93° C. |
| 175 | 6-bromo-4-[2-[4-(t-butyl)phenyl]ethoxy]-quinazoline | 88–90° C. |
| 176 | 4-[2-[[5-(trifluoromethyl)-2-pyridinyl]-thio]ethoxy]quinazoline | 53–55° C. |
| 177 | 6-bromo-N-[2-(4-phenoxyphenyl)ethyl]-4-quinazolinamine | 137–139° C. |
| 178 | 4-[4-[4-(t-butyl)phenyl]butoxy]-quinazoline | oil |
| 179 | 4-(3,3-dimethylbutoxy)quinazoline | oil |
| 180 | 4-[2-(4-butoxyphenyl)ethoxy]quinazoline | 56–58° C. |
| 181 | 4-[2-[2,6-bis(i-propyl)phenoxy]ethoxy]-quinazoline | oil |
| 182 | 4-[2-(3-phenoxyphenyl)propoxy]quinazoline | oil |
| 183 | 4-[2-[(4-quinazolinyl)oxy]ethyl]benzo-nitrile | 153–154 |
| 184 | 4-(nonyloxy)quinazoline | oil |
| 185 | 8-chloro-4-[2-[4-(t-butyl)phenyl]-ethoxy]quinazoline | 115–118° C. |
| 186 | 4-(octadecyloxy)quinazoline | 63–65° C. |
| 187 | 4-[2-(1,1'-biphenyl)-4-ylpropoxy]-quinazoline | oil |
| 188 | 4-[2-[4-[3-(trifluoromethyl)phenoxy]-phenyl]ethoxy]quinazoline | 69–71° C. |
| 189 | 4-[2-[4-(trimethylsilyl)phenyl]ethoxy]-quinazoline | oil |
| 190 | 6-methyl-N-[2-(3-phenoxyphenyl)ethyl]-4-quinazolinamine | 101–103° C. |
| 191 | 4-[2-[4-(trimethylsilyl)phenyl]ethoxy]-quinazoline monohydrochloride | 190° C. |
| 192 | 4-(3-chloro-2,2-dimethylpropoxy)quin-azoline | 45–47° C. |
| 193 | 4-(3-butynyloxy)quinazoline | NA |
| 194 | 4-(3-methylpentyloxy)quinazoline | oil |
| 195 | 8-fluoro-4-[2-[2-(i-propyl)phenyl]-ethoxy]quinazoline | 85–87° C. |
| 196 | 4-[3-(3-trifluoromethylphenyl)propoxy]-quinazoline | 30° C. |
| 197 | 8-fluoro-4-[2-(1,1'-biphenyl)-4-ylbutoxy)-quinazoline | 88–90° C. |
| 198 | 8-fluoro-4-[2-[4-(2-fluorophenoxy)phenyl]-ethoxy]quinazoline | 86–88° C. |
| 199 | 8-fluoro-4-[2-(1,1'-biphenyl)4-ylpropoxy]-quinazoline | 115° C. |
| 200 | 8-fluoro-4-[4-[4-(t-butyl)phenyl]butoxyl-quinazoline | oil |
| 201 | N-[2-(3,4-dimethoxyphenyl)ethyl]-8-fluoro-4-quinazolinamine | 172–174° C. |
| 202 | 6-bromo-4-ethoxyquinazoline | 106–108° C. |
| 203 | 4-ethoxyquinazoline | oil |
| 204 | 4-[2-(2,3-dihydro-1H-inden-5-yl)ethoxy]-quinazoline | oil |
| 205 | 4-[2-[4-[[4-(trifluoromethyl)phenyl]-methoxy]phenyl]ethoxy]quinazoline | 120–122° C. |
| 206 | 4-(2-phenoxyethoxy)quinazoline | 42–44° C. |
| 207 | N-[2-(2,4-difluorophenyl)ethyl]-6-methyl-4-quinazolinamine | 160–162° C. |
| 208 | 4-[2-(4-cyclohexylphenyl)ethoxy]-quinazoline | 38–40° C. |
| 209 | 4-[2-(4-propoxyphenyl)ethoxy]quinazoline | 67–69° C. |
| 210 | 4-[2-(2,5-difluorophenyl)ethoxy]-quinazoline | 82–84° C. |
| 211 | 4-[2-(2-chloro-4-fluorophenyl)ethoxy]-quinazoline | 94–96° C. |
| 212 | N-[2-(2,4-dichlorophenyl)ethyl]-4-quinazolinamine | 189–191° C. |
| 213 | 5-fluoro-4-[2-[4-(t-butyl)phenyl]-ethoxy]quinazoline | 99–101° C. |
| 214 | 4-[2-(2,4-dichlorophenyl)ethoxy]-quinazoline | 112–113° C. |
| 215 | 6-methyl-4-(2-[1,1'-biphenyl-4-yl-ethoxy)quinazoline | 55–57° C. |
| 216 | 4-[2-[4-(t-butyl)phenyl]ethoxy]-5-methylquinazoline | 126–128° C. |
| 217 | N-[2-(4-ethoxyphenyl)ethyl]-4-quinazolinamine | 158–160° C. |
| 218 | 4-[2-(2,4-difluorophenyl)ethoxy]-quinazoline | 60–62° C. |

| EXAMPLE NUMBER | COMPOUND | M.P. |
|---|---|---|
| 219 | N-[2-(4-butoxyphenyl)ethyl]-8-fluoro-4-quinazolinamine | 172–174° C. |
| 220 | N-[2-(4-bromophenyl)ethyl]-4-quinazolinamine | 190–192° C. |
| 221 | 4-[2-(3,4-dichlorophenyl)ethoxy]-8-fluoroquinazoline | 130–132° C. |
| 222 | 4-[2-(2,4-dichlorophenyl)ethoxy]-8-fluoroquinazoline | 100–102° C. |
| 223 | 4-[2-(3-methyl-4-methoxyphenyl)ethoxy]-quinazoline | 73–75° C. |
| 224 | 4-[2-(2,6-dichlorophenyl)ethoxy]-8-fluoroquinazoline | 110–112° C. |
| 225 | 8-fluoro-4-[2-(4-propoxyphenyl)ethoxy]-quinazoline | 79–81° C. |
| 226 | 4-[2-[4-(trifluoromethoxy)phenyl]ethoxy]-quinazoline | 44–46° C. |
| 227 | 4-[2-(5-chloro-1,3-benzodioxol-6-yl)ethoxy]quinazoline | 110–112° C. |
| 228 | 8-methyl-4-(2-[1,1-biphenyl]-4-ylethoxy)-quinazoline | 53–55° C. |
| 229 | N-[2-(3-methoxyphenyl)ethyl]-4-quinazolinamine | 174–176° C. |
| 230 | 8-fluoro-4-[2-(3-methyl-4-methoxyphenyl)-ethoxy]quinazoline | 90–92° C. |
| 231 | 4-[2-(4-chlorophenyl)ethoxy]-5-methyl-quinazoline | 88–90° C. |
| 232 | 8-methyl-4-[2-(4-ethoxyphenyl)ethoxy]-quinazoline | 47–49° C. |
| 233 | 8-methyl-N-[2-(2-naphthyl)ethyl]-4-quinazolinamine | 200–203° C. |
| 234 | N-[2-[4-(heptyloxy)phenyl]ethyl]-4-quinazolinamine | 100–102° C. |
| 235 | 8-fluoro-N-[2-(2,4-difluorophenyl)-ethyl]4-quinazolinamine | 190–200° C. |
| 236 | 8-fluoro-4-[2-(2,5-difluorophenyl)-ethoxy]quinazoline | 115–116° C. |
| 237 | 4-[2-[4-[4-(trifluoromethyl)phenoxy]-phenyl]ethoxy]quinazoline | 53–55° C. |
| 238 | N-[2-(4-chlorophenyl)ethyl]-8-methyl-4-quinazolinamine | 166–168° C. |
| 239 | 8-fluoro-4-[3-[3-(trifluoromethyl)-phenyl]propoxy]quinazoline | 48–50° C. |
| 240 | 4-[2-(6-chloro-1,3-benzodioxol-5-yl)-ethoxy]-8-fluoroquinazoline | 146–148° C. |
| 241 | 8-fluoro-4-[3-(4-ethoxyphenyl)propyl]-quinazoline | oil |
| 242 | N-[2-(4-ethylphenyl)ethyl]-4-quinazolinamine | 157–159° C. |
| 243 | 5-methyl-N-[2-(2-naphthyl)ethyl]-4-quinazolinamine | 90–92° C. |
| 244 | 4-[[4-(ethylthio)phenyl]methoxy]-quinazoline | 84–86° C. |
| 245 | N-[2-[4-(ethylthio)phenyl]ethyl]-4-quinazolinamine | 120–122° C. |
| 246 | N-[2-[4-(propoxy)phenyl]ethyl]-4-quinazolinamine | 148–150° C. |
| 247 | N-[4-[4-(trifluoromethyl)phenyl]butyl]-4-quinazolinamine | 100–102° C. |
| 248 | 4-[2-[4-[[4-(t-butyl)phenyl]methoxy]-phenyl]ethoxy]quinazoline | oil |
| 249 | 8-fluoro-N-[2-(4-propoxyphenyl)ethyl]-4-quinazolinamine | 163–165° C. |
| 250 | 4-[2-(1,3-benzodioxol-5-yl)ethoxy]-quinazoline | 72–74° C. |
| 251 | 4-[2-(1,3-benzodioxol-5-yl)ethoxy]-8-fluoroquinazoline | 101–106° C. |
| 252 | 4-[2,3-dihydro-1H-inden-2-yl)oxy]-quinazoline | 126–128° C. |
| 253 | 4-[2-[4-(3-methylphenoxy)phenyl]ethoxy]-quinazoline | 64–66° C. |
| 254 | 4-[2-(4-methoxyphenoxy)ethoxy]quinazoline | 62–64° C. |
| 255 | N-[2-[4-(1,1,2,2-tetrafluoroethoxy)-phenyl]ethyl]-4-quinazolinamine | 137–139° C. |
| 256 | 8-fluoro-4-[2-[(4-methoxyphenyl)-methoxy]ethoxy]quinazoline | 108–110° C. |
| 257 | 8-fluoro-4-[2-[[4-(t-butyl)phenyl]-methoxyethoxy]quinazoline | 40–42° C. |
| 258 | 4-[2-(9H-fluoren-9-yl)ethoxy]-quinazoline | 90–91° C. |
| 259 | 4-[2-(2-cyclohexylphenyl)ethoxy]-quinazoline | 53–55° C. |
| 260 | 4-[2-(3,4-dichlorophenyl)ethoxy]-quinazoline | 114–115° C. |
| 261 | 4-[2-(2,6-dichlorophenyl)ethoxy]-quinazoline | 132–133° C. |
| 262 | 4-[2-(2,4-dichlorophenoxy)ethoxy]-8-fluoroquinazoline | 83–85° C. |
| 263 | 8-fluoro-4-[2-[3,5-di(trichloromethyl)-phenyl]ethoxy]quinazoline | 129° C. |
| 264 | 4-[(3-cyclohexyl-2-propenyl)oxyl-quinazoline | oil |
| 265 | 4-[2-(2-ethoxyethoxy)ethoxy]quinazoline | oil |

The procedures described in the following detailed examples are representative of the procedures used to prepare the compounds of the other examples.

EXAMPLE 2

4-[2-[4-(t-Butyl)phenyl]ethoxy]quinazoline

To a solution of 1.1 g of sodium hydride in 50 ml of DMF, 4.0 g of 2-[4-(t-butyl)phenyl]ethanol was added, and the mixture was stirred at room temperature for one hour. Then 3.6 g of 4-chloroquinazoline in 20 ml of DMF were added, and the mixture was stirred at room temperature overnight. The mixture was then poured into a mixture of ice in water. The product was extracted into $CH_2Cl_2$, and the resulting solution was concentrated to dryness. TLC showed one major spot and five minor spots. The product was purified by HPLC (silica gel, $CH_2Cl_2$). The fractions containing the major product were collected and concentrated, giving 1.9 g of the title product. Yield: 28.4%. M.P. 70°–71° C.

The compound of Example 2 was prepared on a larger scale, using a preferred process, as follows: To 54 L of methylene chloride, and 1.8 L of pyridine, 6.5 Kg of 4-hydroxyquinazoline was added, and the mixture was cooled to −5° to 10° C. To this mixture 15.7 Kg of triphenyl phosphite was added. Then 3.67 Kg of chlorine gas was bubbled in over a three hour period while the temperature of the mixture was maintained in the range of 0° to 10° C., to produce 4-chloroquinazoline hydrochloride. After stirring the mixture an additional hour, 105 mL of water was added to quench excess halogenating reagent. Then 9.7 Kg of 4-(t-butyl)benzeneethanol was added over a 15 minute period while the mixture was maintained at 10° to 20° C. The mixture was heated to reflux (40°–45° C.) and held at reflux for three hours. After vacuum distilling the contents of the reaction to minimize volume, 56 L of toluene was added. The contents of the reaction were again vacuum distilled, 56 L of heptane were added, and the mixture was cooled to 30°–35° C. The HCl salt of the desired product was isolated by filtration, and washed with toluene/heptane.

The free base was obtained by combining the wet cake of the HCl salt with 58 L acetone and 6.5 L of triethylamine. After heating the mixture to 25°–30° C. the contents of the reaction were vacuum distilled to a volume of 45 L, and then 70 L of water were added. The mixture was cooled to 5°–10° C. over 45 minutes, and the title product was then isolated by filtration. Yield: 11.5 Kg (85%).

EXAMPLE 5

4-[2-(4-Chlorophenyl)ethoxy]quinazoline

To a solution of 1.1 g of sodium hydride in 50 ml of DMF was added 3.4 g of 2-(4-chlorophenyl)ethanol, and the mixture was stirred at room temperature for one hour. Then 3.6 g of 4-chloroquinazoline in 20 ml of DMF were added, and the mixture was stirred overnight. The mixture was then poured into a mixture of ice in water. Solid was collected and recrystallized from pentane giving 0.149 g of the title product. Yield: 2.4%. M.P. 57°–58° C.

EXAMPLE 29

4-(3-phenylpropyl)quinazoline

A mixture of 3.3 g of 4-chloroquinazoline and 4.65 g of 5-(2-phenylethyl) barbituric acid was heated to 170° C. for two and one-half hours, then cooled to form the 5-(2-phenylethyl)-5-(4-quinazolyl) barbituric acid. This compound was hydrolyzed, without isolation, by adding 40 ml of water and 4.5 g of NaOH to the mixture, heating to reflux for four hours. The mixture was cooled, acidified with HCl, refluxed two additional hours, then cooled, and neutralized. Product was extracted into $CH_2Cl_2$, which was then separated, dried, and evaporated. The residue was absorbed onto silica gel and eluted with 10% $EtOAc/CH_2Cl_2 \rightarrow 20\%$ $EtOAc/CH_2Cl_2$. Fractions containing product were combined. TLC showed impurities present. The product was rechromatographed using 15% $EtOAc/CH_2Cl_2$, however, impurities remained. Solvent was evaporated and the residue was redissolved in pentane. The product dissolved in pentane leaving impurities as a gummy residue. The pentane solution was decanted, filtered, and evaporated to give 0.75 g of the title product as a light oil.

EXAMPLE 53

N-[2-(2-naphthyl)ethyl]-4-quinazolinamine

A mixture of 1.0 g of 4-chloroquinazoline and 2.0 g of 2-(2-naphthyl)ethyl amine was heated under nitrogen to 165°–170° C. for one hour. The mixture was cooled and then 200 ml of a 50/50 mixture of ammonium hydroxide/water was added. The product was extracted into $CH_2Cl_2$, and the resulting solution was treated with charcoal and filtered. The solution was then concentrated to dryness, and the residue was recrystallized from a mixture of pentane and $CH_2Cl_2$ to give: 0.480 g of the title product. Yield: 26.7%. M.P. 172°–174° C.

EXAMPLE 74

N,N'-bis[2-(2-thienyl)ethyl]-2,4-quinazolinediamine

A mixture of 1.4 g of 2,4-dichloroquinazoline and 3.5 g of 2-(2-thienyl)ethylamine was stirred under nitrogen at 160°–165° C. for one hour, then cooled. To the mixture 200 ml of a 50/50 mixture of $NH_4OH$/water was added. The product was extracted into $CH_2Cl_2$, and this solution was concentrated to dryness. The residue was purified by HPLC (silica gel, 80% pentane/20% EtOAc) to provide 1.3 g of the title product Yield: 50.0% M.P. oil.

EXAMPLE 85

4-[2-(1,1'-biphenyl)-4-ylethoxy]quinazoline

To a solution of 0.53 g of sodium hydride in 200 ml of DMF was added 2.2 g of 2-[(1,1'-biphenyl)-4-yl]ethanol, and the mixture was stirred at room temperature for one hour. Then 1.8 g of 4-chloroquinazoline in 20 ml of DMF were added, and the mixture was stirred at room temperature for another three hours. The mixture was then poured into a mixture of ice in water. The solid phase was collected and washed with water. TLC showed two spots. The product was purified using HPLC (silica gel, $CH_2Cl_2$) giving 1.1 g of the title product. Yield: 30.6%. M.P. 72°–74° C.

The following is another, preferred process for preparing the title product:

A suspension of 8.2 g of 4-chloroquinazoline and 9.9 g of 2-[(1,1'-biphenyl)-4-yl]ethanol in 250 mL of toluene saturated with HCl gas was heated to 50° C. for four hours. Then an additional 3.6 g of 4-chloroquinazoline were added, and heating to 50° C. was continued for one hour. Then the mixture was cooled, ice water was added, and the pH was adjusted to 8.5 using dilute sodium hydroxide. The toluene layer was separated, washed with brine, and filtered through phase separating paper. The toluene solution was placed in a freezer overnight. A small amount of hydroxyquinazoline crystallized, and was separated by filtration. The toluene solution was concentrated to dryness, and the residue was dissolved in ether, then pentane was added, and the title product crystallized. Yield: 12.3 g (75%). M.P. 71°–72° C.

EXAMPLE 96

8-fluoro-N-[2-[4-(i-propyl)phenyl]ethyl]-4-quinazolinamine

A mixture of 2 g of 4-chloro-8-fluoroquinazoline, 1.94 g of 2-[4-(i-propyl)phenyl]ethylamine, and 1.21 g of triethylamine in 100 mL of ethanol was heated at reflux for one hour. The ethanol was removed and the remaining product was dissolved in 100 mL of methylenechloride and then washed with aqueous sodium carbonate. The organic layer was then dried and the solvent was removed. The residue was slurried in pentane. Yield: 2.4 g. M.P. 170°–172° C.

EXAMPLE 99

8-fluoro-4-[2-(4-methylphenyl)ethoxy]quinazoline

To a mixture of 0.6 g of sodium hydride (50%, suspension in oil) and 2 g of 4-chloro-8-fluoroquinazoline in 20 ml of DMF was added 1.64 g of 2-(4-methylphenyl)ethanol, and the mixture was stirred for one hour. Then the mixture was poured into ice water. The solid was collected by filtration. Yield: 0.7 g (20.5%). M.P. 72°–74° C.

Fungicide Utility

The compounds of the present invention have been found to control fungi, particularly plant pathogens. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

Greenhouse Tests

The following experiments were performed in the laboratory to determine the fungicidal efficacy of the compounds of the invention.

Test 1

This screen was used to evaluate the efficacy of the present compounds against a variety of different organisms that cause plant diseases.

The test compounds were formulated for application by dissolving 50 mg of the compound into 1.25 ml of solvent. The solvent was prepared by mixing 50 ml of "Tween 20" (polyoxyethylene (20) sorbitan monolaurate emulsifier) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Table | Host |
|---|---|---|
| *Erysiphe graminis tritici* (powdery mildew) | POWD MDEW | wheat |
| *Pyricularia oryzae* (rice blast) | RICE BLAS | rice |
| *Puccinia recondita tritici* (leaf rust) | LEAF RUST | wheat |
| *Botrytis cinerea* (gray mold) | GRAY MOLD | grape berries |
| *Pseudoperonospora cubensis* (downy mildew) | DOWN MDEW | squash |
| *Cercospora beticola* (leaf spot) | LEAF SPOT | sugar beet |
| *Venturia inaequalis* (apple scab) | APPL SCAB | apple seedling |
| *Septoria tritici* (leaf blotch) | LEAF BLOT | wheat |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2–4 hours.

Table 1 presents the activity of typical compounds of the present invention when evaluated in this experiment. The effectiveness of test compounds in controlling disease was rated using the following scale.

| | |
|---|---|
| 0 | = not tested against specific organism |
| − | = 0–19% control at 400 ppm |
| + | = 20–89% control at 400 ppm |
| + + | = 90–100% control at 400 ppm |
| + + + | = 90–100% control at 100 ppm |

TABLE 1

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 1 | + | + | + | − | +++ | 0 | 0 | + |
| 2 | ++ | +++ | +++ | − | +++ | ++ | + | + |
| 3 | + | ++ | + | − | ++ | − | − | − |
| 4 | − | + | ++ | − | + | − | − | − |
| 5 | +++ | +++ | +++ | − | + | +++ | +++ | ++ |
| 6 | − | ++ | − | − | + | 0 | 0 | 0 |
| 7 | − | + | − | − | + | 0 | 0 | 0 |
| 8 | +++ | ++ | + | − | ++ | 0 | 0 | 0 |
| 9 | − | − | + | − | ++ | 0 | 0 | 0 |
| 10 | +++ | +++ | +++ | − | +++ | 0 | 0 | 0 |
| 11 | ++ | − | ++ | − | +++ | 0 | 0 | 0 |
| 12 | ++ | + | + | − | − | 0 | 0 | 0 |
| 13 | +++ | +++ | +++ | − | +++ | 0 | 0 | 0 |
| 14 | + | + | + | − | ++ | 0 | 0 | 0 |
| 15 | +++ | +++ | +++ | − | +++ | 0 | 0 | 0 |
| 16 | +++ | +++ | +++ | − | +++ | 0 | 0 | 0 |
| 17 | ++ | +++ | +++ | − | +++ | 0 | 0 | 0 |
| 18 | ++ | + | + | − | ++ | 0 | 0 | 0 |
| 19 | − | + | + | − | − | 0 | 0 | 0 |
| 20 | ++ | ++ | + | − | + | 0 | 0 | 0 |
| 21 | +++ | +++ | +++ | − | +++ | 0 | 0 | 0 |
| 22 | +++ | +++ | +++ | − | +++ | 0 | 0 | 0 |
| 23 | − | + | + | − | + | 0 | 0 | 0 |
| 24 | + | + | + | − | +++ | − | − | − |
| 25 | − | + | + | − | ++ | − | − | − |
| 26 | − | ++ | ++ | − | +++ | + | − | + |
| 27 | − | + | + | − | +++ | − | − | + |
| 28 | − | + | ++ | − | + | − | − | − |
| 29 | + | +++ | ++ | − | ++ | − | + | − |
| 30 | ++ | − | − | − | + | + | − | + |
| 31 | + | +++ | +++ | − | ++ | + | − | +++ |
| 32 | − | − | − | − | + | 0 | 0 | 0 |
| 33 | ++ | − | +++ | − | ++ | 0 | 0 | 0 |
| 34 | − | +++ | ++ | − | +++ | 0 | 0 | 0 |
| 35 | − | +++ | ++ | − | +++ | 0 | 0 | 0 |
| 36 | − | + | − | − | + | 0 | 0 | 0 |
| 37 | − | − | − | − | − | 0 | 0 | 0 |
| 38 | ++ | +++ | +++ | − | +++ | + | + | ++ |

TABLE 1-continued

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 39 | ++ | +++ | +++ | − | +++ | + | − | +++ |
| 40 | +++ | ++ | +++ | − | +++ | 0 | 0 | 0 |
| 41 | +++ | ++ | +++ | − | +++ | 0 | 0 | 0 |
| 42 | +++ | +++ | +++ | − | +++ | 0 | 0 | 0 |
| 43 | ++ | ++ | ++ | − | ++ | 0 | 0 | 0 |
| 44 | − | − | − | − | + | 0 | 0 | 0 |
| 45 | + | − | +++ | − | + | 0 | 0 | 0 |
| 46 | + | +++ | +++ | − | ++ | 0 | 0 | 0 |
| 47 | +++ | +++ | +++ | − | +++ | 0 | 0 | 0 |
| 48 | +++ | + | +++ | − | ++ | 0 | 0 | 0 |
| 49 | +++ | +++ | +++ | − | +++ | 0 | 0 | 0 |
| 50 | +++ | +++ | +++ | − | +++ | 0 | 0 | 0 |
| 51 | ++ | +++ | ++ | − | +++ | 0 | 0 | 0 |
| 52 | +++ | +++ | +++ | − | +++ | +++ | + | +++ |
| 53 | +++ | +++ | +++ | − | +++ | − | + | +++ |
| 54 | ++ | ++ | ++ | − | ++ | + | + | + |
| 55 | +++ | +++ | +++ | − | +++ | 0 | 0 | 0 |
| 56 | +++ | +++ | +++ | − | +++ | 0 | 0 | 0 |
| 57 | − | − | − | − | − | 0 | 0 | 0 |
| 58 | + | + | +++ | − | ++ | 0 | 0 | 0 |
| 59 | − | + | − | − | + | 0 | 0 | 0 |
| 60 | + | +++ | + | − | ++ | 0 | 0 | 0 |
| 61 | − | − | − | − | − | 0 | 0 | 0 |
| 62 | − | + | + | − | ++ | 0 | 0 | 0 |
| 63 | +++ | +++ | +++ | − | +++ | 0 | 0 | 0 |
| 64 | ++ | +++ | + | − | +++ | 0 | 0 | 0 |
| 65 | +++ | +++ | +++ | − | +++ | 0 | 0 | 0 |
| 66 | +++ | +++ | +++ | − | +++ | 0 | 0 | 0 |
| 67 | + | + | − | − | ++ | 0 | 0 | 0 |
| 68 | +++ | +++ | +++ | − | +++ | 0 | 0 | 0 |
| 69 | +++ | +++ | +++ | − | +++ | 0 | 0 | 0 |
| 70 | + | +++ | + | − | + | 0 | 0 | 0 |
| 71 | ++ | +++ | +++ | − | +++ | 0 | 0 | 0 |
| 72 | ++ | + | +++ | − | ++ | 0 | 0 | 0 |
| 73 | ++ | +++ | +++ | − | +++ | 0 | 0 | 0 |
| 74 | − | + | + | − | +++ | − | − | − |
| 75 | + | + | + | +++ | + | − | + | − |
| 76 | +++ | +++ | +++ | − | +++ | 0 | 0 | 0 |
| 77 | − | ++ | ++ | − | − | 0 | 0 | 0 |
| 78 | + | +++ | +++ | − | +++ | 0 | 0 | 0 |
| 79 | + | +++ | ++ | − | +++ | 0 | 0 | 0 |
| 80 | +++ | +++ | +++ | − | +++ | 0 | 0 | 0 |
| 81 | + | ++ | + | − | + | − | + | − |
| 82 | + | ++ | +++ | − | +++ | + | + | − |
| 83 | +++ | + | − | − | + | + | + | + |
| 84 | ++ | ++ | +++ | − | ++ | − | ++ | + |
| 85 | ++ | + | +++ | − | +++ | − | − | +++ |
| 86 | ++ | +++ | +++ | − | +++ | ++ | +++ | ++ |
| 87 | ++ | +++ | ++ | − | +++ | + | − | − |
| 88 | +++ | +++ | +++ | − | +++ | 0 | 0 | 0 |
| 89 | +++ | +++ | +++ | − | +++ | 0 | 0 | 0 |
| 90 | + | + | + | − | +++ | 0 | 0 | 0 |
| 91 | + | ++ | + | − | ++ | 0 | 0 | 0 |
| 92 | + | +++ | +++ | − | +++ | 0 | 0 | 0 |
| 93 | +++ | +++ | +++ | − | +++ | 0 | 0 | 0 |
| 94 | +++ | +++ | +++ | − | +++ | 0 | 0 | 0 |
| 95 | +++ | − | +++ | − | +++ | 0 | 0 | 0 |
| 96 | +++ | +++ | +++ | − | +++ | 0 | 0 | 0 |
| 97 | +++ | ++ | +++ | − | ++ | 0 | 0 | 0 |
| 98 | + | + | + | − | + | 0 | 0 | 0 |
| 99 | +++ | +++ | +++ | − | +++ | 0 | 0 | 0 |
| 100 | +++ | +++ | +++ | − | +++ | 0 | 0 | 0 |
| 101 | + | +++ | +++ | ++ | +++ | 0 | 0 | 0 |
| 102 | ++ | +++ | +++ | ++ | ++ | 0 | 0 | 0 |
| 103 | + | + | +++ | − | + | 0 | 0 | 0 |
| 104 | +++ | +++ | +++ | − | +++ | 0 | 0 | 0 |
| 105 | − | + | ++ | − | − | 0 | 0 | 0 |
| 106 | +++ | +++ | +++ | − | +++ | + | +++ | +++ |
| 107 | + | + | +++ | − | +++ | ++ | − | +++ |
| 108 | + | +++ | + | − | +++ | ++ | − | +++ |
| 109 | − | − | − | − | ++ | + | − | +++ |
| 110 | − | + | ++ | − | + | − | − | − |
| 111 | − | ++ | + | − | + | 0 | 0 | 0 |
| 112 | + | +++ | +++ | − | +++ | 0 | 0 | 0 |
| 113 | + | +++ | +++ | − | +++ | 0 | 0 | 0 |
| 114 | − | − | + | − | + | 0 | 0 | 0 |
| 115 | + | + | +++ | − | + | 0 | 0 | 0 |
| 116 | ++ | +++ | + | − | +++ | 0 | 0 | 0 |
| 117 | +++ | ++ | +++ | − | ++ | 0 | 0 | 0 |
| 118 | +++ | +++ | +++ | − | +++ | 0 | 0 | 0 |

TABLE 1-continued

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 119 | + | ++ | + | − | − | 0 | 0 | 0 |
| 120 | + | + | + | − | ++ | 0 | 0 | 0 |
| 121 | − | − | − | − | − | 0 | 0 | 0 |
| 122 | − | − | − | − | − | 0 | 0 | 0 |
| 123 | − | − | + | − | − | 0 | 0 | 0 |
| 124 | + | − | − | − | − | 0 | 0 | 0 |
| 125 | + | + | + | − | + | 0 | 0 | 0 |
| 126 | + | +++ | + | − | ++ | 0 | 0 | 0 |
| 127 | +++ | +++ | ++ | − | +++ | 0 | 0 | 0 |
| 128 | ++ | + | + | − | + | 0 | 0 | 0 |
| 129 | − | + | − | − | + | 0 | 0 | 0 |
| 130 | + | − | − | − | − | 0 | 0 | 0 |
| 131 | +++ | +++ | +++ | − | +++ | 0 | 0 | 0 |
| 132 | +++ | +++ | +++ | − | +++ | 0 | 0 | 0 |
| 133 | +++ | +++ | +++ | − | + | 0 | 0 | 0 |
| 134 | +++ | +++ | +++ | 0 | 0 | 0 | 0 | 0 |
| 135 | +++ | +++ | +++ | − | +++ | 0 | 0 | 0 |
| 136 | − | − | − | − | − | 0 | 0 | 0 |
| 137 | +++ | +++ | +++ | − | +++ | 0 | 0 | 0 |
| 138 | ++ | + | − | − | ++ | 0 | 0 | 0 |
| 139 | + | +++ | + | − | ++ | 0 | 0 | 0 |
| 140 | + | ++ | + | − | ++ | 0 | 0 | 0 |
| 141 | + | + | + | − | + | 0 | 0 | 0 |
| 142 | + | ++ | + | − | − | 0 | 0 | 0 |
| 143 | + | ++ | − | − | ++ | 0 | 0 | 0 |
| 144 | +++ | +++ | +++ | − | +++ | 0 | 0 | 0 |
| 145 | + | +++ | + | − | ++ | 0 | 0 | 0 |
| 146 | ++ | +++ | ++ | + | +++ | 0 | 0 | 0 |
| 147 | +++ | − | +++ | − | +++ | 0 | 0 | 0 |
| 148 | ++ | ++ | + | − | ++ | 0 | 0 | 0 |
| 149 | ++ | − | − | − | − | 0 | 0 | 0 |
| 150 | − | − | − | − | + | 0 | 0 | 0 |
| 151 | + | − | − | − | − | 0 | 0 | 0 |
| 152 | +++ | + | + | − | + | 0 | 0 | 0 |
| 153 | ++ | − | − | − | − | 0 | 0 | 0 |
| 154 | ++ | +++ | +++ | − | +++ | 0 | 0 | 0 |
| 155 | ++ | +++ | +++ | − | +++ | 0 | 0 | 0 |
| 156 | +++ | +++ | +++ | − | +++ | 0 | 0 | 0 |
| 157 | +++ | +++ | +++ | ++ | +++ | 0 | 0 | 0 |
| 158 | + | ++ | + | − | ++ | 0 | 0 | 0 |
| 159 | +++ | +++ | +++ | − | +++ | 0 | 0 | 0 |
| 160 | + | +++ | ++ | − | +++ | 0 | 0 | 0 |
| 161 | + | + | ++ | − | − | 0 | 0 | 0 |
| 162 | +++ | +++ | +++ | − | +++ | 0 | 0 | 0 |
| 163 | +++ | +++ | +++ | − | +++ | 0 | 0 | 0 |
| 164 | + | +++ | +++ | − | +++ | 0 | 0 | 0 |
| 165 | + | ++ | ++ | − | ++ | 0 | 0 | 0 |
| 166 | + | ++ | +++ | − | + | 0 | 0 | 0 |
| 167 | + | +++ | + | − | − | 0 | 0 | 0 |
| 168 | +++ | +++ | + | − | ++ | 0 | 0 | 0 |
| 169 | + | +++ | ++ | − | +++ | 0 | 0 | 0 |
| 170 | +++ | +++ | +++ | − | +++ | 0 | 0 | 0 |
| 171 | +++ | +++ | +++ | − | +++ | 0 | 0 | 0 |
| 172 | − | − | − | − | − | 0 | 0 | 0 |
| 173 | ++ | +++ | + | − | + | 0 | 0 | 0 |
| 174 | + | ++ | − | − | ++ | 0 | 0 | 0 |
| 175 | − | ++ | + | − | − | 0 | 0 | 0 |
| 176 | + | ++ | − | − | + | 0 | 0 | 0 |
| 177 | − | +++ | +++ | + | +++ | 0 | 0 | 0 |
| 178 | ++ | − | − | + | + | 0 | 0 | 0 |
| 179 | − | − | − | − | − | 0 | 0 | 0 |
| 180 | +++ | +++ | +++ | − | +++ | 0 | 0 | 0 |
| 181 | ++ | + | − | − | + | 0 | 0 | 0 |
| 182 | ++ | − | ++ | − | − | 0 | 0 | 0 |
| 183 | + | ++ | +++ | − | + | 0 | 0 | 0 |
| 184 | ++ | ++ | − | − | + | 0 | 0 | 0 |
| 185 | + | ++ | + | − | ++ | 0 | 0 | 0 |
| 186 | − | − | − | − | − | 0 | 0 | 0 |
| 187 | − | +++ | + | − | + | 0 | 0 | 0 |
| 188 | +++ | +++ | +++ | − | +++ | 0 | 0 | 0 |
| 189 | +++ | − | +++ | − | +++ | 0 | 0 | 0 |
| 190 | +++ | +++ | +++ | − | +++ | 0 | 0 | 0 |
| 191 | − | − | − | − | − | 0 | 0 | 0 |
| 192 | − | − | − | − | ++ | 0 | 0 | 0 |
| 193 | − | + | − | − | − | 0 | 0 | 0 |
| 194 | − | − | − | − | − | 0 | 0 | 0 |
| 195 | +++ | +++ | +++ | − | ++ | 0 | 0 | 0 |
| 196 | ++ | − | − | − | − | 0 | 0 | 0 |
| 197 | + | + | − | − | − | 0 | 0 | 0 |
| 198 | +++ | +++ | +++ | − | +++ | 0 | 0 | 0 |

TABLE 1-continued

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 199 | +++ | + | +++ | − | + | 0 | 0 | 0 |
| 200 | +++ | +++ | + | − | +++ | 0 | 0 | 0 |
| 201 | + | +++ | + | − | +++ | 0 | 0 | 0 |
| 202 | − | − | ++ | − | ++ | 0 | 0 | 0 |
| 203 | + | − | − | − | + | 0 | 0 | 0 |
| 204 | +++ | ++ | +++ | − | +++ | 0 | 0 | 0 |
| 205 | + | ++ | +++ | − | + | 0 | 0 | 0 |
| 206 | + | ++ | ++ | − | ++ | 0 | 0 | 0 |
| 207 | + | − | +++ | − | +++ | 0 | 0 | 0 |
| 208 | +++ | + | +++ | − | +++ | 0 | 0 | 0 |
| 209 | +++ | ++ | +++ | − | +++ | 0 | 0 | 0 |
| 210 | +++ | +++ | +++ | − | +++ | 0 | 0 | 0 |
| 211 | ++ | +++ | +++ | − | + | 0 | 0 | 0 |
| 212 | + | ++ | +++ | − | − | 0 | 0 | 0 |
| 213 | + | − | + | − | + | 0 | 0 | 0 |
| 214 | + | ++ | − | − | + | 0 | 0 | 0 |
| 215 | +++ | + | +++ | − | +++ | 0 | 0 | 0 |
| 216 | − | + | − | − | + | 0 | 0 | 0 |
| 217 | + | ++ | +++ | − | +++ | 0 | 0 | 0 |
| 218 | +++ | +++ | +++ | + | +++ | 0 | 0 | 0 |
| 219 | ++ | +++ | +++ | − | +++ | 0 | 0 | 0 |
| 220 | + | ++ | +++ | − | − | 0 | 0 | 0 |
| 221 | + | +++ | +++ | − | +++ | 0 | 0 | 0 |
| 222 | +++ | ++ | +++ | − | +++ | 0 | 0 | 0 |
| 223 | + | ++ | ++ | − | ++ | 0 | 0 | 0 |
| 224 | − | − | ++ | − | ++ | 0 | 0 | 0 |
| 225 | ++ | − | ++ | − | ++ | 0 | 0 | 0 |
| 226 | ++ | ++ | ++ | − | ++ | 0 | 0 | 0 |
| 227 | + | − | ++ | − | ++ | 0 | 0 | 0 |
| 228 | ++ | − | ++ | − | − | 0 | 0 | 0 |
| 229 | ++ | − | ++ | − | ++ | 0 | 0 | 0 |
| 230 | ++ | ++ | ++ | − | ++ | 0 | 0 | 0 |
| 231 | ++ | − | +++ | − | ++ | 0 | 0 | 0 |
| 232 | ++ | − | ++ | − | ++ | 0 | 0 | 0 |
| 233 | − | − | ++ | − | ++ | 0 | 0 | 0 |
| 234 | ++ | − | ++ | − | ++ | 0 | 0 | 0 |
| 235 | ++ | − | ++ | − | ++ | 0 | 0 | 0 |
| 236 | ++ | − | ++ | − | ++ | 0 | 0 | 0 |
| 237 | ++ | + | ++ | − | ++ | 0 | 0 | 0 |
| 238 | + | + | ++ | − | ++ | 0 | 0 | 0 |
| 239 | ++ | − | ++ | − | + | 0 | 0 | 0 |
| 240 | + | − | ++ | − | ++ | 0 | 0 | 0 |
| 241 | ++ | − | ++ | − | ++ | 0 | 0 | 0 |
| 246 | + | +++ | +++ | − | +++ | 0 | 0 | 0 |
| 247 | +++ | +++ | +++ | − | +++ | 0 | 0 | 0 |
| 248 | − | ++ | + | − | + | 0 | 0 | 0 |
| 249 | ++ | +++ | +++ | − | +++ | 0 | 0 | 0 |
| 250 | +++ | +++ | +++ | − | +++ | 0 | 0 | 0 |
| 251 | +++ | +++ | + | − | +++ | 0 | 0 | 0 |
| 252 | + | ++ | +++ | − | +++ | 0 | 0 | 0 |
| 253 | ++ | ++ | +++ | − | +++ | 0 | 0 | 0 |
| 254 | + | + | ++ | − | ++ | 0 | 0 | 0 |
| 255 | ++ | + | +++ | − | +++ | 0 | 0 | 0 |
| 256 | + | + | ++ | − | ++ | 0 | 0 | 0 |
| 257 | ++ | + | + | − | +++ | 0 | 0 | 0 |
| 258 | − | − | − | − | + | 0 | 0 | 0 |
| 259 | + | − | − | − | − | 0 | 0 | 0 |
| 260 | − | + | ++ | − | + | 0 | 0 | 0 |
| 261 | + | + | − | − | − | 0 | 0 | 0 |
| 262 | − | + | − | − | − | 0 | 0 | 0 |
| 263 | + | + | − | − | − | 0 | 0 | 0 |
| 264 | ++ | − | + | − | − | 0 | 0 | 0 |
| 265 | + | ++ | + | − | − | 0 | 0 | 0 |

Field Tests

Selected compounds were field tested on various crops against a variety of pathogens. Table 2 identifies pathogens against which given compounds demonstrated activity in these field tests.

TABLE 2

| COMPOUND EX. NO. | CROP | PATHOGEN |
|---|---|---|
| 2 | barley | *Erysiphe graminis hordei* |
| | | *Pyrenophora teres* |
| | | *Rhynchosporium secalis* |
| | cucumber | *Sphaerotheca fuliginea* |
| | grape | *Plasmopara viticola* |
| | sugar beet | *Erysiphe sp.* |
| | wheat | *Erysiphe graminis tritici* |
| | | *Pseudocercosporella herpotrichoides* |
| 5 | grape | *Plasmopara viticola* |
| | potato | *Phytophthora infestans* |
| 53 | apple | *Podosphaera leucotricha* |
| | barley | *Erysiphe graminis hordei* |
| | | *Pyrenophora teres* |

TABLE 2-continued

| COMPOUND EX. NO. | CROP | PATHOGEN |
|---|---|---|
| | cucumber | Rhynchosporium secalis |
| | | Sphaerotheca fuliginea |
| | grapes | Plasmopara viticola |
| | | Uncinula necator |
| | rape | Alternaria brassicae |
| | wheat | Septoria nodorum |
| | | Erysiphe graminis tritici |
| | | Pseudocercosporella herpotrichoides |

Combinations

Fungal disease pathogens are known to develop resistance to fungicides. When strains resistant to a fungicide do develop, it becomes necessary to apply larger and larger amounts of the fungicide to obtain desired results. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (1) in combination with a second fungicide.

Contemplated classes of fungicides from which the second fungicide may be selected include:
1) N-substituted azoles, for example propiconazole, triademefon, flusilazol, diniconazole, ethyltrianol, myclobutanil, and prochloraz;
2) pyrimidines, such as fenarimol and nuarimol;
3) morpholines, such as fenpropimorph and tridemorph;
4) piperazines, such as triforine; and
5) pyridines, such as pyrifenox.

Fungicides in these five classes all function by inhibiting sterol biosynthesis. Additional classes of contemplated fungicides, which have other mechanisms of action include:
6) dithiocarbamates, such as maneb and mancozeb;
7) phthalimides, such as captafol;
8) isophthalonitrites, such as chlorothalonil;
9) dicarboximides, such as iprodione;
10) benzimidazoles, such as benomyl and carbendazim;
11) 2-aminopyrimidines, such as ethirimol;
12) carboxamides, such as carboxin; and
13) dinitrophenols, such as dinocap.

The fungicide combinations of the invention contain at least 1%, ordinarily 20 to 80%, and more typically 50 to 75% by weight of a compound of formula (1).

Insecticide and Miticide Utility

The compounds of the invention are also useful for the control of insects and mites. Therefore, the present invention also is directed to a method for inhibiting an insect or mite which comprises applying to a locus of the insect or mite an insect- or mite-inhibiting amount of a compound of formula (1).

The compounds of the invention show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

Representative mite species with which it is contemplated that the present invention can be practiced include those listed below.

| FAMILY | SCIENTIFIC NAME | COMMON NAME |
|---|---|---|
| ACARIDAE | Aleurobius farinae | |
| | Rhizoglyphus echinopus | Bulb mite |
| | Rhizoglyphus elongatus | |
| | Rhizoglyphus rhizophagus | |
| | Rhizoglyphus sagittatae | |
| | Rhizoglyphus tarsalis | |
| ERIOPHYIDAE | Abacarus farinae | Grain rust mite |
| | Aceria brachytarsus | |
| | Acalitus essigi | Redberry mite |
| | Aceria ficus | |
| | Aceria fraaxinivorus | |
| | Aceria granati | |
| | Aceria parapopuli | |
| | Eriophyes sheldoni | Citrus bud mite |
| | Aceria tulipae | |
| | Aculus carnutus | Peach silver mite |
| | Aculus schlechtendali | Apple rust mite |
| | Colomerus vitis | Grape erineum mite |
| | Eriophyes convolvens | |
| | Eriophyes insidiosus | |
| | Eriophyes malifoliae | |
| | Eriophyes padi | |
| | Eriophyes pruni | |
| | Epitrimerus pyri | Pear leaf blister mite |
| | Eriophyes ramosus | |
| | Eriophyes sheldoni | Citrus bud mite |
| | Eriophyes ribis | |
| | Phyllocoptes gracilis | Dryberry mite |
| | Phyllocoptruta oleivora | Citrus rust mite |
| | Phytoptus ribis | |
| | Trisetacus pini | |
| | Vasates amygdalina | |
| | Vasates eurynotus | |
| | Vasates quadripedes | Maple bladdergall mite |
| | Vasates schlechtendali | |
| EUPODIDAE | Penthaleus major | Winter grain mite |
| | Linopodes spp. | |
| NALEPELLIDAE | Phylocoptella avellanae | Filbert bud mite |
| PENTHALEIDAE | Halotydeus destrustor | |
| PYEMOTIDAE | Pyemotes tritici | Straw itch mite |
| | Siteroptes cerealium | |
| TARSONEMIDAE | Polyphagotarsonemus latus | Broad mite |
| | Steneotarsonemus pallidus | Cyclamen mite |
| TENUIPALPIDAE | Brevipalpus californicus | |
| | Brevipalpus obovatus | Privet mite |
| | Brevipalpus lewisi | Citrus flat mite |
| | Dolichotetranychus floridanus | Pineapple flase spider mite |
| | Tenuipalpes granati | |
| | Tenuipalpes pacificus | |
| TETRANYCHIDAE | Bryobia arborea | |
| | Bryobia practiosa | Clover mite |
| | Bryobia rubrioculus | Brown mite |
| | Eotetranychus coryli | |
| | Eotetranychus hicoriae | Pecan deaf scorch mite |
| | Eotetranychus lewisi | |
| | Eotetranychus sexmaculatus | Sixspotted spider mite |

-continued

| FAMILY | SCIENTIFIC NAME | COMMON NAME |
|---|---|---|
| | *Eotetranychus willametti* | |
| | *Eotetranychus banksi* | Texas citrus mite |
| | *Oligonychus ilicis* | Southern red mite |
| | *Oligonychus pratensis* | Banks grass mite |
| | *Oligonychus ununguis* | Spruce spider mite |
| | *Panonychus citri* | Citrus red mite |
| | *Panonychus ulmi* | European red mite |
| | *Paratetranychus modestus* | |
| | *Paratetranychus pratensis* | |
| | *Paratetranychus viridis* | |
| | *Petrobia latens* | Brown wheat mite |
| | *Schizotetranychus celarius* | Bamboo spider mite |
| | *Schizotetranychus pratensis* | |
| | *Tetranychus canadensis* | Fourspotted spider mite |
| | *Tetranychus cinnabarinus* | Carmine spider mite |
| | *Tetranychus mcdanieli* | McDaniel spider mite |
| | *Tetranychus pacificus* | Pacific spider mite |
| | *Tetranychus schoenei* | Schoene spider mite |
| | *Tetranychus urticae* | Twospotted spider mite |
| | *Tetranychus turkestani* | Strawberry spider mite |
| | *Tetranychus desertorum* | Desert spider mite |

The compounds are useful for reducing populations of insects and mites, and are used in a method of inhibiting an insect or mite population which comprises applying to a locus of the insect or arachnid an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts, which the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites; or a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm active compound is used.

In a preferred embodiment, the present invention is directed to a method for inhibiting a mite which comprises applying to a plant an effective mite-inactivating amount of a compound of formula (1) in accordance with the present invention.

MITE/INSECT SCREEN

The compounds of Examples 1–203 were tested for miticidal and insecticidal activity in the following mite-/insect screen.

Each test compound was formulated by dissolving the compound in acetone/alcohol (50:50) mixture containing 23 g of "TOXIMUL R" (sulfonate/nonionic emulsifier blend) and 13 g of "TOXIMUL S" (sulfonate/nonionic emulsifier blend) per liter. These mixtures were then diluted with water to give the indicated concentrations.

Twospotted spider mites (*Tetranychus urticae* Koch) and melon aphids (*Aphis gossypii* Glover) were introduced on squash cotyledons and allowed to establish on both leaf surfaces. Other plants in the same treatment pot were left uninfested. The leaves were then sprayed with 5 ml of test solution using a DeVilbiss atomizing sprayer at 10 psi. Both surfaces of the leaves were covered until runoff, and then allowed to dry for one hour. Two uninfested leaves were then excised and placed into a Petri dish containing larval southern armyworm (*Spodopetra eridania* Cramer).

Activity on Southern corn rootworm (*Diabrotica undecimpuctata howardi* Barber) was evaluated by adding two ml of tap water, a presoaked corn seed, and 15 g of dry sandy soil to a one ounce plastic container. The soil was treated with 1 mL of test solution containing a predetermined concentration of test compound. After six to 12 hours of drying, five 2–3 instar corn rootworm larvae were added to the individual cups, which were then capped and held at 23° C.

After standard exposure periods, percent mortality and phytotoxicity were evaluated. Results for the compounds found to be active are reported in Table 3. The remaining compounds showed no activity. The following abbreviations are used in Table 3:

CRW refers to corn rootworm
SAW refers to Southern armyworm
SM refers to twospotted spider mites
MA refers to melon aphids.

TABLE 3

| | | | Mite/Insect Screen | | | |
|---|---|---|---|---|---|---|
| COMPOUND | CRW RATE PPM | CRW RESULTS % | SAW SM & MA RATE PPM | SAW RESULTS % | SM RESULTS % | MA RESULTS % |
| 1 | 12.00 | 0 | 200 | 0 | 0 | 0 |
| 2 | 24.00 | 0 | 400 | 20 | 90 | 80 |
|   | 12.00 | 0 | 200 | 0 | 100 | 90 |
| 3 | 12.00 | 0 | 200 | 0 | 0 | 0 |
|   | 24.00 | 0 | 400 | 0 | 50 | 100 |
| 4 | 24.00 | 0 | 400 | 0 | 0 | 0 |
|   | 12.00 | 0 | 200 | 0 | 0 | 0 |
| 5 | 24.00 | 0 | 400 | 0 | 50 | 100 |
|   | 12.00 | 0 | 200 | 20 | 100 | 100 |
| 6 | 24.00 | 0 | 400 | 0 | 0 | 0 |
|   | 12.00 | 0 | 200 | 0 | 0 | 0 |

TABLE 3-continued

Mite/Insect Screen

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| 7 | 12.00 | 0 | 200 | 0 | 0 | 0 |
|  | 24.00 | 0 | 400 | 0 | 0 | 0 |
| 8 | 12.00 | 0 | 200 | 0 | 0 | 0 |
|  | 24.00 | 0 | 400 | 0 | 0 | 0 |
| 9 | 24.00 | 0 | 400 | 0 | 0 | 0 |
| 10 | 24.00 | 0 | 400 | 100 | 0 | 0 |
| 11 | 24.00 | 0 | 400 | 0 | 0 | 0 |
| 12 | 24.00 | 0 | 400 | 0 | 0 | 0 |
|  | 12.00 | 0 | 200 | 100 | 50 | 50 |
| 13 | 24.00 | 0 | 400 | 0 | 90 | 90 |
| 14 | 24.00 | 0 | 400 | 0 | 0 | 0 |
| 15 | 24.00 | 0 | 400 | 0 | 0 | 0 |
| 16 | 24.00 | 0 | 400 | 0 | 0 | 0 |
| 17 | 24.00 | 0 | 400 | 0 | 100 | 100 |
| 18 | 24.00 | 100 | 400 | 0 | 0 | 0 |
| 19 | 24.00 | 0 | 400 | 0 | 0 | 0 |
| 20 | 24.00 | 100 | 400 | 60 | 100 | 100 |
| 21 | 24.00 | 100 | 400 | 0 | 60 | 80 |
| 22 | 24.00 | 0 | 400 | 0 | 20 | 80 |
| 23 | 24.00 | 0 | 400 | 0 | 0 | 0 |
|  | 12.00 | 0 | 200 | 0 | 0 | 0 |
| 24 | 12.00 | 0 | 200 | 0 | 0 | 0 |
| 25 | 12.00 | 0 | 200 | 0 | 0 | 0 |
| 26 | 12.00 | 0 | 200 | 0 | 0 | 0 |
| 27 | 12.00 | 0 | 200 | 0 | 0 | 0 |
| 28 | 12.00 | 0 | 200 | 0 | 0 | 0 |
| 29 | 24.00 | 0 | 400 | 0 | 80 | 80 |
| 30 | 12.00 | 0 | 200 | 0 | 30 | 80 |
|  | 24.00 | 0 | 400 | 0 | 50 | 50 |
| 31 | 24.00 | 0 | 400 | 30 | 0 | 0 |
|  | 12.00 | 0 | 200 | 80 | 0 | 40 |
| 32 | 24.00 | 0 | 400 | 0 | 0 | 0 |
|  | 12.00 | 0 | 200 | 0 | 0 | 0 |
| 33 | 24.00 | 80 | 400 | 0 | 80 | 100 |
|  | 12.00 | 0 | 200 | 0 | 50 | 80 |
| 34 | 24.00 | 0 | 400 | 0 | 0 | 0 |
|  | 12.00 | 0 | 200 | 0 | 0 | 0 |
| 35 | 24.00 | 0 | 400 | 80 | 0 | 0 |
|  | 12.00 | 0 | 200 | 20 | 0 | 0 |
| 36 | 24.00 | 0 | 400 | 0 | 0 | 0 |
|  | 12.00 | 0 | 200 | 0 | 0 | 0 |
| 37 | 24.00 | 0 | 400 | 0 | 0 | 0 |
|  | 12.00 | 0 | 200 | 0 | 0 | 0 |
| 38 | 24.00 | 100 | 400 | 40 | 90 | 80 |
|  | 12.00 | 0 | 200 | 40 | 0 | 0 |
| 39 | 24.00 | 0 | 400 | 0 | 0 | 0 |
| 40 | 24.00 | 0 | 400 | 0 | 90 | 0 |
|  | 12.00 | 0 | 200 | 40 | 80 | 20 |
| 41 | 24.00 | 0 | 400 | 0 | 80 | 80 |
| 42 | 24.00 | 0 | 400 | 50 | 100 | 100 |
|  | 12.00 | 0 | 200 | 0 | 100 | 100 |
| 43 | 24.00 | 0 | 400 | 0 | 0 | 0 |
| 44 | 24.00 | 0 | 400 | 0 | 0 | 0 |
| 45 | 24.00 | 0 | 400 | 0 | 0 | 0 |
| 46 | 24.00 | 0 | 400 | 0 | 0 | 0 |
| 47 | 24.00 | 0 | 400 | 0 | 0 | 0 |
| 48 | 24.00 | 0 | 400 | 0 | 90 | 100 |
| 49 | 24.00 | 0 | 400 | 0 | 80 | 0 |
| 50 | 24.00 | 100 | 400 | 0 | 90 | 90 |
| 51 | 24.00 | 0 | 400 | 0 | 0 | 0 |
| 52 | 12.00 | 0 | 200 | 0 | 0 | 0 |
|  | 12.00 | 0 | 200 | 90 | 0 | 0 |
| 53 | 12.00 | 0 | 200 | 0 | 0 | 0 |
|  | 12.00 | 0 | 200 | 20 | 0 | 0 |
| 54 | 12.00 | 0 | 200 | 0 | 0 | 0 |
| 55 | 24.00 | 0 | 400 | 0 | 0 | 0 |
|  | 12.00 | 0 | 200 | 100 | 100 | 100 |
| 56 | 24.00 | 0 | 400 | 0 | 0 | 0 |
|  | 12.00 | 0 | 200 | 0 | 40 | 100 |
| 57 | 24.00 | 0 | 400 | 0 | 0 | 0 |
|  | 12.00 | 0 | 200 | 80 | 0 | 0 |
| 58 | 24.00 | 0 | 400 | 0 | 0 | 0 |
|  | 12.00 | 0 | 200 | 100 | 0 | 0 |
| 59 | 24.00 | 0 | 400 | 0 | 0 | 0 |
| 60 | 24.00 | 0 | 400 | 0 | 100 | 100 |
| 61 | 24.00 | 0 | 400 | 0 | 0 | 0 |
|  | 12.00 | 0 | 200 | 0 | 0 | 0 |

TABLE 3-continued

| | | | Mite/Insect Screen | | | |
|---|---|---|---|---|---|---|
| COMPOUND | CRW RATE PPM | CRW RESULTS % | SAW SM & MA RATE PPM | SAW RESULTS % | SM RESULTS % | MA RESULTS % |
| 62 | 24.00 | 100 | 400 | 0 | 0 | 80 |
| | 12.00 | 0 | 200 | 0 | 0 | 0 |
| 63 | 24.00 | 0 | 400 | 0 | 100 | 100 |
| 64 | 24.00 | 0 | 400 | 0 | 90 | 70 |
| 65 | 24.00 | 0 | 400 | 0 | 100 | 100 |
| 66 | 24.00 | 0 | 400 | 0 | 0 | 0 |
| 67 | 24.00 | 0 | 400 | 0 | 60 | 30 |
| 68 | 24.00 | 0 | 400 | 0 | 90 | 100 |
| 69 | 24.00 | 0 | 400 | 100 | 100 | 0 |
| 70 | 24.00 | 0 | 400 | 0 | 80 | 0 |
| 71 | 24.00 | 0 | 400 | 60 | 0 | 0 |
| 72 | 24.00 | 0 | 400 | 100 | 0 | 0 |
| 73 | 24.00 | 100 | 400 | 0 | 0 | 0 |
| 74 | 12.00 | 0 | 200 | 0 | 0 | 0 |
| 75 | 12.00 | 0 | 200 | 0 | 0 | 0 |
| 76 | 24.00 | 100 | 400 | 80 | 90 | 100 |
| | 12.00 | 100 | 200 | 100 | 0 | 0 |
| 77 | 24.00 | 0 | 400 | 0 | 0 | 0 |
| | 12.00 | 0 | 200 | 0 | 0 | 0 |
| 78 | 24.00 | 100 | 400 | 80 | 0 | 0 |
| | 12.00 | 0 | 200 | 100 | 0 | 0 |
| 79 | 24.00 | 0 | 400 | 0 | 0 | 0 |
| | 12.00 | 0 | 200 | 0 | 50 | 50 |
| 80 | 24.00 | 100 | 400 | 0 | 100 | 100 |
| 81 | 12.00 | 0 | 200 | 0 | 50 | 0 |
| | 24.00 | 0 | 400 | 0 | 0 | 0 |
| 82 | 12.00 | 0 | 200 | 0 | 20 | 80 |
| | 24.00 | 0 | 400 | 0 | 0 | 0 |
| 83 | 12.00 | 0 | 200 | 30 | 0 | 0 |
| | 24.00 | 0 | 400 | 40 | 0 | 0 |
| 84 | 24.00 | 40 | 400 | 0 | 0 | 0 |
| | 12.00 | 0 | 200 | 0 | 0 | 0 |
| 85 | 12.00 | 0 | 200 | 10 | 100 | 100 |
| | 24.00 | 0 | 400 | 80 | 100 | 100 |
| 86 | 12.00 | 0 | 200 | 30 | 0 | 50 |
| | 24.00 | 0 | 400 | 0 | 0 | 80 |
| 87 | 24.00 | 0 | 400 | 50 | 90 | 100 |
| | 12.00 | 0 | 200 | 0 | 90 | 100 |
| 88 | 24.00 | 0 | 400 | 100 | 0 | 0 |
| | 12.00 | 0 | 200 | 0 | 100 | 100 |
| 89 | 12.00 | 0 | 200 | 0 | 0 | 0 |
| | 24.00 | 0 | 400 | 0 | 0 | 0 |
| 90 | 24.00 | 0 | 400 | 100 | 0 | 0 |
| | 12.00 | 0 | 200 | 0 | 100 | 80 |
| 91 | 24.00 | 0 | 400 | 0 | 0 | 0 |
| 92 | 24.00 | 0 | 400 | 0 | 0 | 0 |
| | 12.00 | 0 | 200 | 0 | 0 | 0 |
| 93 | 24.00 | 0 | 400 | 100 | 0 | 0 |
| | 12.00 | 0 | 200 | 100 | 80 | 80 |
| 94 | 24.00 | 0 | 400 | 100 | 0 | 0 |
| | 12.00 | 0 | 200 | 100 | 100 | 80 |
| 95 | 24.00 | 0 | 400 | 0 | 0 | 0 |
| | 12.00 | 0 | 200 | 0 | 0 | 80 |
| 96 | 24.00 | 0 | 400 | 100 | 0 | 0 |
| | 12.00 | 0 | 200 | 100 | 50 | 50 |
| 97 | 24.00 | 0 | 400 | 0 | 0 | 0 |
| 98 | 24.00 | 0 | 400 | 0 | 0 | 0 |
| 99 | 24.00 | 0 | 400 | 0 | 0 | 0 |
| | 12.00 | 0 | 200 | 0 | 100 | 100 |
| 100 | 24.00 | 100 | 400 | 0 | 0 | 0 |
| | 12.00 | 0 | 200 | 80 | 80 | 80 |
| 101 | 24.00 | 0 | 400 | 0 | 100 | 100 |
| | 12.00 | 100 | 200 | 100 | 100 | 80 |
| 102 | 24.00 | 0 | 400 | 100 | 90 | 90 |
| | 12.00 | 0 | 200 | 80 | 80 | 80 |
| 103 | 24.00 | 0 | 400 | 0 | 0 | 0 |
| 104 | 24.00 | 100 | 400 | 100 | 0 | 0 |
| 105 | 24.00 | 0 | 400 | 0 | 0 | 0 |
| 106 | 12.00 | 0 | 200 | 90 | 100 | 0 |
| | 24.00 | 0 | 400 | 80 | 80 | 80 |
| 107 | 12.00 | 0 | 200 | 30 | 0 | 0 |
| | 24.00 | 0 | 400 | 0 | 0 | 0 |
| 108 | 12.00 | 0 | 200 | 0 | 60 | 30 |
| | 24.00 | 0 | 400 | 0 | 90 | 20 |
| 109 | 12.00 | 0 | 200 | 0 | 0 | 0 |
| | 24.00 | 0 | 400 | 0 | 0 | 0 |
| 110 | 12.00 | 0 | 200 | 0 | 0 | 0 |

TABLE 3-continued

Mite/Insect Screen

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| | 24.00 | 0 | 400 | 0 | 0 | 0 |
| 111 | 12.00 | 0 | 200 | 0 | 0 | 0 |
| | 24.00 | 0 | 400 | 0 | 0 | 0 |
| 112 | 12.00 | 0 | 200 | 0 | 0 | 80 |
| | 24.00 | 0 | 400 | 0 | 0 | 0 |
| 113 | 12.00 | 0 | 200 | 0 | 100 | 100 |
| | 24.00 | 0 | 400 | 40 | 0 | 0 |
| 114 | 12.00 | 0 | 200 | 0 | 0 | 60 |
| | 24.00 | 0 | 400 | 0 | 0 | 0 |
| 115 | 12.00 | 0 | 200 | 0 | 0 | 0 |
| | 24.00 | 0 | 400 | 0 | 0 | 0 |
| 116 | 12.00 | 0 | 200 | 0 | 0 | 0 |
| | 24.00 | 0 | 400 | 0 | 0 | 0 |
| 117 | 12.00 | 0 | 200 | 0 | 100 | 90 |
| | 24.00 | 0 | 400 | 0 | 0 | 0 |
| 118 | 12.00 | 0 | 200 | 60 | 100 | 100 |
| | 24.00 | 0 | 400 | 100 | 0 | 0 |
| 119 | 12.00 | 0 | 200 | 0 | 50 | 80 |
| | 24.00 | 0 | 400 | 90 | 0 | 0 |
| 120 | 12.00 | 0 | 200 | 0 | 10 | 30 |
| | 24.00 | 0 | 400 | 0 | 0 | 0 |
| 121 | 12.00 | 0 | 200 | 0 | 0 | 0 |
| | 24.00 | 0 | 400 | 0 | 0 | 0 |
| 122 | 12.00 | 0 | 200 | 0 | 0 | 0 |
| | 24.00 | 0 | 400 | 60 | 0 | 0 |
| 123 | 12.00 | 0 | 200 | 0 | 0 | 0 |
| | 24.00 | 0 | 400 | 100 | 0 | 0 |
| 124 | 12.00 | 0 | 200 | 0 | 50 | 80 |
| | 24.00 | 0 | 400 | 0 | 0 | 0 |
| 125 | 12.00 | 0 | 200 | 0 | 0 | 0 |
| | 24.00 | 0 | 400 | 0 | 0 | 0 |
| 126 | 12.00 | 0 | 200 | 0 | 100 | 100 |
| | 24.00 | 0 | 400 | 0 | 100 | 80 |
| 127 | 12.00 | 0 | 200 | 0 | 100 | 100 |
| | 24.00 | 0 | 400 | 0 | 100 | 100 |
| 128 | 12.00 | 0 | 200 | 0 | 0 | 0 |
| | 24.00 | 0 | 400 | 0 | 0 | 0 |
| 129 | 12.00 | 0 | 200 | 0 | 0 | 0 |
| | 24.00 | 0 | 400 | 0 | 80 | 100 |
| 130 | 12.00 | 0 | 200 | 0 | 80 | 80 |
| | 24.00 | 0 | 400 | 0 | 70 | 100 |
| 131 | 24.00 | 0 | 400 | 0 | 0 | 0 |
| 132 | 12.00 | 0 | 200 | 0 | 20 | 80 |
| | 24.00 | 0 | 400 | 0 | 0 | 0 |
| 133 | 12.00 | 0 | 200 | 0 | 0 | 0 |
| | 12.00 | 0 | 200 | 0 | 100 | 80 |
| | 24.00 | 100 | 400 | 0 | 100 | 100 |
| 134 | 12.00 | 0 | 200 | 60 | 90 | 100 |
| | 24.00 | 0 | 400 | 100 | 100 | 100 |
| 135 | 12.00 | 0 | 200 | 0 | 0 | 0 |
| | 24.00 | 0 | 400 | 0 | 0 | 0 |
| 136 | 12.00 | 0 | 200 | 100 | 0 | 0 |
| | 24.00 | 0 | 400 | 0 | 0 | 0 |
| 137 | 12.00 | 0 | 200 | 0 | 0 | 60 |
| | 24.00 | 100 | 400 | 0 | 0 | 0 |
| 138 | 12.00 | 0 | 200 | 0 | 0 | 30 |
| | 24.00 | 0 | 400 | 0 | 80 | 60 |
| 139 | 12.00 | 0 | 200 | 0 | | 30 |
| | 24.00 | 0 | 400 | 0 | 100 | 0 |
| 140 | 12.00 | 0 | 200 | 0 | 0 | 0 |
| | 24.00 | 0 | 400 | 0 | 80 | 0 |
| 141 | 24.00 | 0 | 400 | 0 | 0 | 0 |
| 142 | 24.00 | 0 | 400 | 0 | 60 | 30 |
| 143 | 12.00 | 0 | 200 | 80 | 0 | 0 |
| | 24.00 | 0 | 400 | 0 | 0 | 0 |
| 144 | 12.00 | 100 | 200 | 40 | | 60 |
| | 24.00 | 40 | 400 | 0 | 100 | 100 |
| 145 | 12.00 | 0 | 200 | 0 | 80 | 80 |
| | 24.00 | 0 | 400 | 0 | 0 | 80 |
| 146 | 12.00 | 0 | 200 | 0 | 100 | 100 |
| | 24.00 | 0 | 400 | 0 | 60 | 80 |
| 147 | 12.00 | 0 | 200 | 0 | 0 | 50 |
| | 24.00 | 0 | 400 | 0 | 0 | 0 |
| 148 | 24.00 | 0 | 400 | 0 | 0 | 0 |
| 149 | 12.00 | 0 | 200 | 0 | 0 | 0 |
| | 24.00 | 0 | 400 | 0 | 0 | 0 |
| 150 | 12.00 | 0 | 200 | 0 | 0 | 0 |

TABLE 3-continued

Mite/Insect Screen

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| | 24.00 | 80 | 400 | 0 | 70 | 100 |
| 151 | 12.00 | 0 | 200 | 0 | 0 | 80 |
| | 24.00 | 0 | 400 | 0 | 0 | 0 |
| 152 | 12.00 | 0 | 200 | 0 | 90 | 40 |
| | 24.00 | 0 | 400 | 0 | 60 | 80 |
| 153 | 12.00 | 0 | 200 | 0 | 0 | 0 |
| | 24.00 | 0 | 400 | 0 | 90 | 90 |
| 154 | 12.00 | 0 | 200 | 0 | 0 | 0 |
| | 24.00 | 0 | 400 | 0 | 100 | 100 |
| 155 | 12.00 | 0 | 200 | 0 | 100 | 100 |
| | 24.00 | 0 | 400 | 0 | 100 | 100 |
| 156 | 12.00 | 0 | 200 | 60 | 100 | 100 |
| | 24.00 | 0 | 400 | 0 | 80 | 100 |
| 157 | 12.00 | 40 | 200 | 0 | 0 | 0 |
| | 24.00 | 100 | 400 | 0 | 0 | 0 |
| 158 | 12.00 | 0 | 200 | 0 | 0 | 0 |
| | 24.00 | 0 | 400 | 0 | 60 | 40 |
| 159 | 12.00 | 0 | 200 | 0 | 90 | 80 |
| | 24.00 | 0 | 400 | 0 | 80 | 100 |
| 160 | 12.00 | 0 | 200 | 0 | 0 | 0 |
| | 24.00 | 0 | 400 | 0 | 0 | 0 |
| 161 | 12.00 | 0 | 200 | 20 | 70 | 30 |
| | 24.00 | 100 | 400 | 100 | 0 | 0 |
| 162 | 12.00 | 0 | 200 | 60 | 100 | 80 |
| | 24.00 | 100 | 400 | 0 | 100 | 80 |
| 163 | 12.00 | 0 | 200 | 80 | 0 | 80 |
| | 24.00 | 100 | 400 | 100 | 0 | 80 |
| 164 | 12.00 | 0 | 200 | 40 | 80 | 80 |
| | 24.00 | 0 | 400 | 40 | 20 | 80 |
| 165 | 12.00 | 0 | 200 | 0 | 0 | 50 |
| | 24.00 | 0 | 400 | 0 | 0 | 80 |
| 166 | 12.00 | 0 | 200 | 0 | 0 | 0 |
| | 24.00 | 0 | 400 | 0 | 0 | 60 |
| 167 | 12.00 | 0 | 200 | 0 | 90 | 90 |
| | 24.00 | 0 | 400 | 0 | 80 | 80 |
| 168 | 12.00 | 0 | 200 | 0 | 0 | 0 |
| | 24.00 | 0 | 400 | 0 | 0 | 80 |
| 169 | 24.00 | 0 | 400 | 0 | 0 | 0 |
| 170 | 12.00 | 0 | 200 | 0 | 20 | 80 |
| | 24.00 | 0 | 400 | 100 | 100 | 100 |
| 171 | 12.00 | 0 | 200 | 0 | 20 | 80 |
| | 24.00 | 0 | 400 | 0 | 40 | 80 |
| 172 | 12.00 | 100 | 200 | 0 | 0 | 40 |
| | 24.00 | 0 | 400 | 0 | 0 | 0 |
| 173 | 12.00 | 0 | 200 | 0 | 0 | 80 |
| | 24.00 | 0 | 400 | 0 | 0 | 0 |
| 174 | 12.00 | 0 | 200 | 0 | 80 | 0 |
| | 24.00 | 100 | 400 | 0 | 40 | 0 |
| 175 | 12.00 | 0 | 200 | 100 | 60 | 80 |
| | 24.00 | 0 | 400 | 0 | 0 | 0 |
| 176 | 12.00 | 0 | 200 | 0 | 0 | 0 |
| | 24.00 | 0 | 400 | 0 | 0 | 0 |
| 177 | 12.00 | 0 | 200 | 0 | 0 | 80 |
| | 24.00 | 0 | 400 | 0 | 50 | 50 |
| 178 | 12.00 | 0 | 200 | 0 | 40 | 80 |
| | 24.00 | 0 | 400 | 0 | 100 | 100 |
| 179 | 12.00 | 0 | 200 | 60 | 100 | 100 |
| | 24.00 | 0 | 400 | 0 | 60 | 60 |
| 180 | 12.00 | 0 | 200 | 0 | 80 | 50 |
| | 24.00 | 0 | 400 | 100 | 100 | 100 |
| 181 | 12.00 | 0 | 200 | 0 | 0 | 60 |
| | 24.00 | 0 | 400 | 0 | 40 | 50 |
| 182 | 12.00 | 0 | 200 | 0 | 0 | 80 |
| | 24.00 | 0 | 400 | 0 | 80 | 100 |
| 183 | 12.00 | 0 | 200 | 0 | 0 | 0 |
| | 24.00 | 80 | 400 | 0 | 0 | 0 |
| 184 | 12.00 | 0 | 200 | 0 | 80 | 80 |
| | 24.00 | 0 | 400 | 0 | 90 | 100 |
| 185 | 12.00 | 0 | 200 | 0 | 80 | 50 |
| | 24.00 | 0 | 400 | 0 | 30 | 30 |
| 186 | 12.00 | 0 | 200 | 0 | 0 | 0 |
| | 24.00 | 0 | 400 | 0 | 0 | 0 |
| 187 | 12.00 | 0 | 200 | 0 | 0 | 0 |
| | 24.00 | 0 | 400 | 0 | 0 | 0 |
| 188 | 12.00 | 0 | 200 | 0 | 100 | 100 |
| | 24.00 | 100 | 400 | 80 | | 80 |
| 189 | 12.00 | 0 | 200 | 0 | 80 | 100 |

TABLE 3-continued

Mite/Insect Screen

| COMPOUND | CRW RATE PPM | CRW RESULTS % | SAW SM & MA RATE PPM | SAW RESULTS % | SM RESULTS % | MA RESULTS % |
|---|---|---|---|---|---|---|
|  | 24.00 | 0 | 400 | 0 | 100 | 100 |
| 190 | 12.00 | 0 | 200 | 0 | 80 | 40 |
|  | 24.00 | 0 | 400 | 0 | 0 | 0 |
| 191 | 12.00 | 0 | 200 | 80 | 100 | 100 |
|  | 24.00 | 0 | 400 | 0 | 80 | 80 |
| 192 | 12.00 | 0 | 200 | 0 | 0 | 0 |
|  | 24.00 | 0 | 400 | 0 | 0 | 0 |
| 193 | 12.00 | 0 | 200 | 0 | 0 | 0 |
|  | 24.00 | 0 | 400 | 0 | 0 | 0 |
| 194 | 12.00 | 0 | 200 | 0 | 20 | 30 |
|  | 24.00 | 0 | 400 | 0 | 0 | 80 |
| 195 | 12.00 | 0 | 200 | 0 | 0 | 80 |
|  | 24.00 | 0 | 400 | 0 | 0 | 0 |
| 196 | 12.00 | 0 | 200 | 0 | 0 | 0 |
|  | 24.00 | 0 | 400 | 0 | 0 | 0 |
| 197 | 12.00 | 0 | 200 | 0 | 80 | 80 |
|  | 24.00 | 0 | 400 | 0 | 0 | 0 |
| 198 | 12.00 | 0 | 200 | 100 | 100 | 100 |
|  | 24.00 | 0 | 400 | 100 | 0 | 0 |
| 199 | 12.00 | 0 | 200 | 0 | 100 | 100 |
|  | 24.00 | 0 | 400 | 60 | 0 | 0 |
| 200 | 12.00 | 100 | 200 | 0 | 80 | 60 |
|  | 24.00 | 100 | 400 | 0 | 100 | 80 |
| 201 | 12.00 | 0 | 200 | 0 | 30 | 40 |
|  | 24.00 | 0 | 400 | 0 | 0 | 0 |
| 202 | 12.00 | 0 | 200 | 0 | 50 | 50 |
|  | 24.00 | 0 | 400 | 0 | 0 | 80 |
| 204 | 24.00 | 0 | 400 | 80 | 100 | 100 |
| 205 | 12.00 | 0 | 200 | 0 | 0 | 0 |
|  | 24.00 | 0 | 400 | 0 | 0 | 80 |
| 206 | 12.00 | 0 | 200 | 0 | 0 | 0 |
|  | 24.00 | 0 | 400 | 0 | 0 | 30 |
| 207 | 12.00 | 100 | 200 | 0 | 0 | 0 |
|  | 24.00 | 100 | 400 | 0 | 0 | 0 |
| 208 | 12.00 | 60 | 200 | 100 | 100 | 100 |
|  | 24.00 | 0 | 400 | 100 | 100 | 100 |
| 209 | 12.00 | 0 | 200 | 100 | 100 | 100 |
|  | 24.00 | 0 | 400 | 100 | 100 | 100 |
| 210 | 12.00 | 0 | 200 | 0 | 0 | 80 |
|  | 24.00 | 0 | 400 | 0 | 0 | 0 |
| 211 | 12.00 | 0 | 200 | 0 | 40 | 80 |
|  | 24.00 | 0 | 400 | 0 | 60 | 80 |
| 212 | 12.00 | 0 | 200 | 0 | 0 | 0 |
|  | 24.00 | 0 | 400 | 0 | 0 | 0 |
| 213 | 12.00 | 0 | 200 | 0 | 80 | 80 |
|  | 24.00 | 0 | 400 | 0 | 0 | 0 |
| 214 | 12.00 | 100 | 200 | 0 | 0 | 0 |
|  | 24.00 | 0 | 400 | 0 | 0 | 0 |
| 215 | 12.00 | 0 | 200 | 0 | 100 | 100 |
|  | 24.00 | 0 | 400 | 0 | 100 | 100 |
| 216 | 12.00 | 0 | 200 | 0 | 100 | 100 |
|  | 24.00 | 0 | 400 | 0 | 0 | 0 |
| 217 | 12.00 | 0 | 200 | 50 | 90 | 0 |
|  | 24.00 | 0 | 400 | 0 | 0 | 0 |
| 218 | 12.00 | 100 | 200 | 20 | 80 | 100 |
|  | 24.00 | 100 | 400 | 0 | 100 | 100 |
| 219 | 12.00 | 60 | 200 | 0 | 0 | 0 |
|  | 24.00 | 0 | 400 | 80 | 90 | 80 |
| 220 | 12.00 | 100 | 200 | 80 | 0 | 0 |
|  | 24.00 | 100 | 400 | 0 | 0 | 0 |
| 221 | 12.00 | 0 | 200 | 0 | 60 | 100 |
|  | 24.00 | 100 | 400 | 0 | 0 | 0 |
| 222 | 12.00 | 0 | 200 | 0 | 0 | 100 |
|  | 24.00 | 0 | 400 | 0 | 0 | 100 |
| 223 | 12.00 | 0 | 200 | 0 | 100 | 100 |
|  | 24.00 | 0 | 400 | 0 | 80 | 100 |
| 224 | 12.00 | 0 | 200 | 0 | 0 | 0 |
|  | 24.00 | 0 | 400 | 0 | 0 | 0 |
| 225 | 12.00 | 0 | 200 | 0 | 100 | 100 |
|  | 24.00 | 0 | 400 | 80 | 0 | 0 |
| 226 | 12.00 | 0 | 200 | 40 | 100 | 100 |
|  | 24.00 | 0 | 400 | 100 | 100 | 100 |
| 227 | 12.00 | 0 | 200 | 0 | 80 | 90 |
|  | 24.00 | 0 | 400 | 0 | 0 | 0 |
| 228 | 12.00 | 0 | 200 | 0 | 100 | 100 |
|  | 24.00 | 0 | 400 | 0 | 40 | 0 |
| 229 | 12.00 | 0 | 200 | 0 | 0 | 0 |

TABLE 3-continued

Mite/Insect Screen

| COMPOUND | CRW RATE PPM | CRW RESULTS % | SAW SM & MA RATE PPM | SAW RESULTS % | SM RESULTS % | MA RESULTS % |
|---|---|---|---|---|---|---|
|  | 24.00 | 0 | 400 | 0 | 0 | 0 |
| 230 | 12.00 | 0 | 200 | 0 | 100 | 100 |
|  | 24.00 | 0 | 400 | 0 | 100 | 100 |
| 231 | 12.00 | 100 | 200 | 0 | 90 | 90 |
|  | 24.00 | 100 | 400 | 0 | 0 | 0 |
| 232 | 12.00 | 0 | 200 | 0 | 90 | 90 |
|  | 24.00 | 0 | 400 | 0 | 80 | 100 |
| 233 | 12.00 | 0 | 200 | 0 | 0 | 0 |
|  | 24.00 | 0 | 400 | 0 | 0 | 0 |
| 234 | 12.00 | 0 | 200 | 40 | 0 | 0 |
|  | 24.00 | 80 | 400 | 0 | 0 | 0 |
| 235 | 12.00 | 100 | 200 | 20 | 0 | 0 |
|  | 24.00 | 20 | 400 | 0 | 0 | 0 |
| 236 | 12.00 | 0 | 200 | 0 | 0 | 0 |
|  | 24.00 | 0 | 400 | 0 | 0 | 0 |
| 237 | 24.00 | 100 | 400 | 80 | 80 | 100 |
| 238 | 12.00 | 0 | 200 | 0 | 0 | 0 |
|  | 24.00 | 0 | 400 | 0 | 0 | 0 |
| 239 | 12.00 | 0 | 200 | 0 | 0 | 0 |
|  | 24.00 | 0 | 400 | 0 | 0 | 0 |
| 240 | 12.00 | 0 | 200 | 0 | 0 | 0 |
|  | 24.00 | 0 | 400 | 0 | 0 | 0 |
| 241 | 12.00 | 0 | 200 | 0 | 100 | 100 |
|  | 24.00 | 0 | 400 | 0 | 100 | 80 |
| 242 | 24.00 | 100 | 400 | 0 | 80 | 30 |
| 246 | 12.00 | 100 | 200 | 0 | 40 | 80 |
|  | 24.00 | 0 | 400 | 0 | 0 | 0 |
| 247 | 24.00 | 0 | 400 | 0 | 0 | 0 |
| 248 | 24.00 | 0 | 400 | 0 | 0 | 0 |
| 249 | 12.00 | 60 | 200 | 0 | 0 | 100 |
|  | 24.00 | 100 | 400 | 100 | 80 | 80 |
| 250 | 12.00 | 60 | 200 | 0 | 0 | 100 |
|  | 24.00 | 0 | 400 | 0 | 0 | 40 |
| 251 | 24.00 | 0 | 400 | 0 | 0 | 0 |
| 252 | 24.00 | 0 | 400 | 0 | 0 | 0 |
| 253 | 12.00 | 0 | 200 | 100 | 100 | 100 |
|  | 24.00 | 0 | 400 | 80 | 100 | 100 |
| 254 | 12.00 | 0 | 200 | 0 | 0 | 0 |
|  | 24.00 | 60 | 400 | 0 | 0 | 0 |
| 255 | 12.00 | 0 | 200 | 100 | 100 | 100 |
|  | 24.00 | 0 | 400 | 80 | 80 | 60 |
| 256 | 12.00 | 0 | 200 | 0 | 0 | 0 |
|  | 24.00 | 0 | 400 | 0 | 0 | 0 |
| 257 | 12.00 | 0 | 200 | 0 | 0 | 0 |
|  | 24.00 | 100 | 400 | 0 | 90 | 60 |
| 258 | 12.00 | 0 | 200 | 0 | 0 | 0 |
|  | 24.00 | 0 | 400 | 0 | 0 | 0 |
| 259 | 24.00 | 0 | 400 | 0 | 0 | 0 |
| 260 | 12.00 | 0 | 200 | 0 | 0 | 0 |
|  | 24.00 | 0 | 400 | 0 | 80 | 0 |
| 261 | 12.00 | 0 | 200 | 0 | 0 | 0 |
|  | 24.00 | 0 | 400 | 0 | 0 | 0 |
| 262 | 24.00 | 0 | 400 | 0 | 0 | 0 |
| 263 | 24.00 | 0 | 400 | 0 | 0 | 0 |
| 264 | 24.00 | 0 | 400 | 0 | 0 | 0 |
| 265 | 12.00 | 0 | 200 | 0 | 0 | 40 |
|  | 24.00 | 0 | 400 | 0 | 80 | 60 |

Field Trials

4-[2-[4-(t-butyl)phenyl]ethoxy]quinazoline and 4-[2-(1,1'-biphenyl)-4-ylethoxy]quinazoline were evaluated against a variety of mite and insect species in field trials. The following table reports the plants on which these compounds were tested, and the mite or insect species against which they showed activity.

| PLANT | PEST |
|---|---|
| alfalfa (Lucerne) | pea aphid, potato leafhopper, tarnished plant bug, green cloverworm |
| apples | apple aphid, European red mite, green peach aphid, white apple leafhopper, apple rust mite, rosy apple aphid |
| azaleas | greenhouse thrips |
|  | twospotted spider mite |
| barley | cereal aphid |
| bean, faba broad | bean aphid |
| broccoli | twospotted spider mite |
| cotton | cotton aphid |
| grape (European) | grape thrips, grape leafhopper |
| hops | Dawson-hop aphid |
| lemon | black citrus aphid |
| pecan nut | yellow hickory aphid |
| pea, garden (English) | pea aphid |

| PLANT | PEST |
| --- | --- |
| plum (Japanese) | twospotted spider mite |
| privet | thrips |
| sugar beet | green peach aphid |
| turnip | potato aphid |
| wheat | wheat aphid |

In addition 4-[2-[4-(t-butyl)phenyl]ethoxy]quinazoline was tested on grapefruit, showing activity against citrus rust mite; and 4-[2-(1,1'-biphenyl)-4-ylethoxy]quinazoline was tested on tomato, showing activity against glasshouse whitefly.

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention have been prepared, and are typical of compositions useful in the practice of the present invention.

| A. 0.75 Emulsifiable Concentrate | |
|---|---|
| 4-[2-[4-(t-butyl)phenyl]ethoxy]quinazoline | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |
| B. 1.5 Emulsifiable Concentrate | |
| 4-[2-[4-(t-butyl)phenyl]ethoxy]quinazoline | 18.50% |
| "TOXIMUL D" | 2.50% |
| "TOXIMUL H" | 2.50% |
| "EXXON 200" | 76.50% |
| C. 0.75 Emulsifiable Concentrate | |
| 4-[2-(1,1'-biphenyl)-4-ylethoxy]quinazoline | 9.38% |
| "TOXIMUL D" | 2.50% |
| "TOXIMUL H" | 2.50% |
| "EXXON 200" | 85.62% |
| D. 1.0 Emulsifiable Concentrate | |
| 4-[2-(1,1'-biphenyl)-4-ylethoxy]quinazoline | 12.50% |
| N-methylpyrrolidone | 25.00% |
| "TOXIMUL D" | 2.50% |
| "TOXIMUL H" | 2.50% |
| "EXXON 200" | 57.50% |
| E. 1.0 Aqueous Suspension | |
| 4-[2-[4-(t-butyl)phenyl]ethoxy]quinazoline | 12.00% |
| "PLURONIC P-103" (block copolymer of propylene oxide and ethylene oxide, surfactant) | 1.50% |
| "PROXEL GXL" (biocide/preservative) | .05% |
| "AF-100" (silicon based antifoam agent) | .20% |
| "REAX 88B" (lignosulfonate dispersing agent) | 1.00% |
| propylene glycol | 10.00% |
| veegum | .75% |
| xanthan | .25% |
| water | 74.25% |
| F. 1.0 Aqueous Suspension | |
| N-[2-(2-naphthyl)ethyl]-4-quinazolinamine | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| G. 1.0 Aqueous Suspension | |
| 4-[2-(1,1'-biphenyl)-4-ylethoxy]quinazoline | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |
| H. Wettable Powder | |
| 4-[2-[4-(t-butyl)phenyl]ethoxy]quinazoline | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| I. Aqueous Suspension | |
| 8-fluoro-4-[2-[4-phenoxyphenyl]ethoxy]quinazoline | 12.40% |
| "TERGITOL 158-7" | 5.00% |
| "ZEOSYL 200" | 1.00% |
| "AF-100" | 0.20% |
| "POLYFON H" | 0.50% |
| 2% xanthan solution | 10.00% |
| tap water | 70.90% |
| J. Emulsifiable Concentrate | |
| 8-fluoro-4-[2-(4-methoxyphenyl)ethoxy]quinazoline | 12.40% |
| "TOXIMUL D" | 2.50% |
| "TOXIMUL H" | 2.50% |
| "EXXON 200" | 82.60% |
| K. Wettable Powder | |
| 8-fluoro-4-[2-(4-methoxyphenyl)ethoxy]quinazoline | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| L. Emulsifiable Concentrate | |
| 4-[2-(4-ethoxyphenyl)ethoxy]quinazoline | 6.19% |
| "TOXIMUL H" | 3.60% |
| "TOXIMUL D" | 0.40% |
| "EXXON 200" | 89.81% |
| M. Wettable Powder | |
| 4-[2-(4-ethoxyphenyl)ethoxy]quinazoline | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| N. Aqueous Suspension | |
| N-[2-[3-(trifluoromethyl)phenyl]ethyl]-8-fluoro-4-quinazolinamine | 12.40% |
| "TERGITOL 158-7" | 5.00% |
| "ZEOSYL 200" | 1.00% |
| "POLYFON H" | 0.50% |
| "AF-100" | 0.20% |
| xanthan solution (2%) | 10.00% |
| tap water | 70.90% |

We claim:

1. A compound of the formula (1)

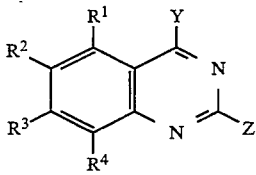

wherein $R^1$ to $R^4$ are independently H, halo, ($C_1$–$C_4$) alkyl, branched ($C_3$–$C_4$) alkyl, halo ($C_1$–$C_4$) alkyl, halo ($C_1$–$C_4$) alkoxy, ($C_1$–$C_4$) alkoxy, halo ($C_1$–$C_4$) alkylthio, OH, CN, $NO_2$, or $NH_2$, at least two of $R^1$ to $R^4$ being H;

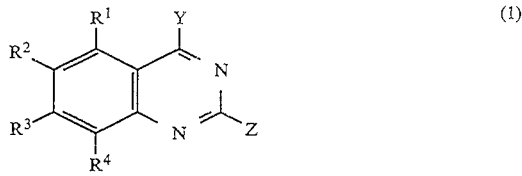

(1)

wherein
$R^1$ to $R^4$ are independently H, halo, ($C_1$-$C_4$) alkyl, branched ($C_3$-$C_4$) alkyl, halo ($C_1$-$C_4$) alkyl, ($C_1$-$C_4$) alkoxy, $NO_2$, or $NH_2$,
provided that
at least two of $R^1$ to $R^4$ are H;
Y is X—W—Ar,
X is O, or $NR^7$, or $CR^8R^9$;
Z is H, Cl, $OCH_3$, $CH_3$, or $CCl_3$;
$R^7$ is H, ($C_1$-$C_4$) alkyl, or acetyl;
$R^8$ and $R^9$ are independently H, ($C_1$-$C_4$)alkyl, ($C_1$-$C_4$) acyl, halo or OH, or $R^8$ and $R^9$ combine to form a saturated or unsaturated carbocyclic ring comprising three to seven carbon atoms;
W is an alkylene chain 2 to 8 carbon atoms long, that optionally includes a saturated or unsaturated carbocyclic ring comprising three to seven carbon atoms, and optionally is substituted with ($C_1$-$C_3$) alkyl, ($C_2$-$C_4$) alkenyl, phenyl, ($C_3$-$C_8$) cycloalkyl, halo, hydroxy, or acetyl; and
Ar is
imidazolyl,
indolyl,
thienyl, optionally substituted with $CH_3$ or Cl,
thiazolyl,
1,3-benzodioxolyl,
fluorenyl,
cyclopentyl,
1-methylcyclopentyl,
cyclohexyl (hexahydrophenyl),
cyclohexenyl (tetrahydrophenyl),
naphthyl,
substituted naphthyl,
dihydronaphthyl,
tetrahydronaphthyl,
decahydronaphthyl,
pyridyl,
substituted pyridyl,
2,3-dihydroindenyl,
or a group of the formula (2):

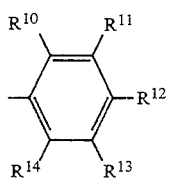

(2)

where
$R^{10}$ to $R^{14}$ are independently H, halo, I, ($C_1$-$C_{10}$) alkyl, branched ($C_3$-$C_6$) alkyl, halo ($C_1$-$C_7$) alkyl, ($C_1$-$C_7$) alkoxy, halo ($C_1$-$C_7$) alkoxy, phenoxy, substituted phenoxy, phenyl, substituted phenyl, phenylthio, substituted phenylthio, $NH_2$, $NO_2$, OH, acetoxy, CN, $SiR^{15}R^{16}R^{17}$, $OSiR^{15}R^{16}R^{17}$, where $R^{15}$, $R^{16}$, and $R^{17}$ are independently $C_1$-$C_4$ alkyl, $C_3$-$C_4$ branched alkyl, phenyl, or substituted phenyl, at least two of $R^{10}$ to $R^{14}$ being H;
or an acid addition salt of a compound of formula (1);
provided that:
(a) if Y is $NR^7$—W—Ar, then $R^4$ is F, or Ar is naphthyl or a group of formula (2) wherein at least one of $R^{10}$ to $R^{14}$ is phenyl, substituted phenyl, phenoxy, substituted phenoxy, phenylthio, substituted phenylthio, halo ($C_1$-$C_4$) alkyl, or halo ($C_1$-$C_4$) alkoxy; and
(b) the compound 4-(3-phenylpropyl)quinazoline is excluded.

2. A compound of the formula (1)

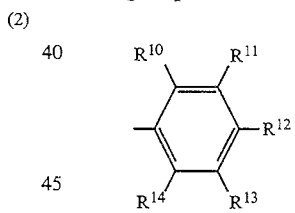

(1)

wherein
$R^1$ to $R^4$ are independently H, halo, ($C_1$-$C_4$) alkyl, branched ($C_3$-$C_4$) alkyl, halo ($C_1$-$C_4$) alkyl, ($C_1$-$C_4$) alkoxy, $NO_2$, or $NH_2$,
provided that
at least two of $R^1$ to $R^4$ are H;
Y is X—W—Ar,
X is O, or $NR^7$;
Z is H, Cl, $OCH_3$, $CH_3$, or $CCl_3$;
$R^7$ is H, ($C_1$-$C_4$) alkyl, or acetyl;
W is an alkylene chain 2 to 6 carbon atoms long, optionally including a carbocyclic ring or substituted with ($C_1$-$C_3$) alkyl, phenyl, ($C_3$-$C_8$) cycloalkyl, halo, hydroxy, or acetyl; and
Ar is
imidazolyl,
indolyl,
thienyl, optionally substituted with $CH_3$ or Cl,
thiazolyl,
1,3-benzodioxolyl,
fluorenyl,
cyclohexyl (hexahydrophenyl),
cyclohexenyl (tetrahydrophenyl),
naphthyl,
dihydronaphthyl,
tetrahydronaphthyl,
decahydronaphthyl,
or a group of the formula (2):

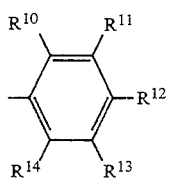

(2)

where
$R^{10}$ to $R^{14}$ are independently H, halo, I, ($C_1$-$C_{10}$) alkyl, branched ($C_3$-$C_6$) alkyl, halo ($C_1$-$C_4$) alkyl, ($C_1$-$C_4$) alkoxy, halo ($C_1$-$C_4$) alkoxy, phenoxy, substituted phenoxy, phenyl, substituted phenyl, phenylthio, substituted phenylthio, $NH_2$, $NO_2$, OH, or CN, at least two of $R^{10}$ to $R^{14}$ being H;
or an acid addition salt of a compound of formula (1);
provided that:
if Y is $NR^7$—W—Ar, then
Ar is naphthyl or a group of formula (2) wherein at least one of $R^{10}$ to $R^{14}$ is phenyl, substituted phenyl, phenoxy, substituted phenoxy, phenylthio, substituted phenylthio, halo($C_1$-$C_4$)alkyl, or halo($C_1$-$C_4$)alkoxy.

3. A compound of claim 1 wherein Y is O—W—Ar.
4. A compound of claim 3 wherein Z is H.
5. A compound of claim 3 wherein W is —$(CH_2)_2$—.
6. A compound of claim 3 wherein $R^4$ is F and the rest of $R^1$ to $R^4$ are H.
7. A compound of claim 3 wherein $R^1$ to $R^4$ are all H.

8. A compound of claim 3 wherein Ar is naphthyl or a phenyl group of formula (2) wherein one of $R^{10}$ to $R^{14}$ is Cl, Br, ($C_1$-$C_{10}$) alkyl, halo ($C_1$-$C_4$) alkyl, ($C_1$-$C_4$) alkoxy, ($C_1$-$C_4$) alkylthio, halo ($C_1$-$C_4$) alkoxy, branched ($C_3$-$C_6$) alkyl, phenyl, substituted phenyl, phenoxy, substituted phenoxy, phenylthio, or substituted phenylthio, and the rest of $R^{10}$ to $R^{14}$ are H.

9. A compound of claim 8 wherein Ar is a phenyl group of formula (12) wherein $R^{12}$ is ethoxy, propoxy, or butoxy.

10. A compound of claim 8 wherein Ar is 2-naphthyl.

11. A compound of claim 8 wherein Ar is (1,1'-biphenyl)-4-yl.

12. A compound of claim 8 wherein Ar is a phenyl group of formula (12) wherein one of $R^{10}$ to $R^{12}$ is branched ($C_3$-$C_6$) alkyl.

13. A compound of claim 8 wherein Ar is a phenyl group of formula (12) wherein one of $R^{10}$ to $R^{12}$ is halo ($C_1$-$C_4$) alkyl.

14. A compound of claim 8 wherein Ar is a phenyl group of formula (2) wherein $R^{12}$ is other than H and $R^{10}$, $R^{11}$, $R^{13}$, and $R^{14}$ are H.

15. A compound of claim 8 which is 4-[2-(2-naphthyl)ethoxy]quinazoline.

16. A compound of claim 8 which is 4-[2-[4-(t-butyl)phenyl]ethoxy]quinazoline.

17. A compound of claim 8 which is 4-[2-(4-chlorophenyl)ethoxy]quinazoline.

18. A compound of claim 8 which is 4-[2-(4-chlorophenyl)ethoxy]-8-fluoroquinazoline.

19. A compound of claim 8 which is 4-(2-[1,1'-biphenyl]-4-ylethoxy)quinazoline.

20. A compound of claim 8 which is 4-[2-(4-methylphenyl)ethoxy]quinazoline.

21. A compound of claim 8 which is 4-[2-[4-(i-propyl)phenyl]ethoxy]quinazoline.

22. A compound of claim 8 which is 8-fluoro-4-[2-(1,1'-biphenyl)-4-ylethoxy]quinazoline.

23. A compound of claim 8 which is 8-fluoro-4-[2-[4-(t-butyl)phenyl]ethoxy]quinazoline.

24. A compound of claim 8 which is 8-fluoro-N-[2-(4-phenoxyphenyl)ethyl]-4-quinazolinamine.

25. A compound of claim 8 which is 8-fluoro-4-[2-(4-methoxyphenyl)ethoxy]quinazoline.

26. A compound of claim 8 which is 4-[2-(4-ethoxyphenyl)ethoxy]quinazoline.

27. A compound of claim 1 wherein Y is —$NR^7$—W—Ar.

28. A compound of claim 27 wherein Z is H.

29. A compound of claim 27 wherein W is —$(CH_2)_2$—.

30. A compound of claim 27 wherein $R^4$ is F and the rest of $R^1$ to $R^4$ are H.

31. A compound of claim 27 wherein Ar is naphthyl or a phenyl group of formula (2) wherein one of $R^{10}$ to $R^{14}$ is Cl, Br, ($C_1$-$C_{10}$) alkyl, halo ($C_1$-$C_4$) alkyl, ($C_1$-$C_4$) alkoxy, ($C_1$-$C_4$) alkylthio, halo ($C_1$-$C_4$) alkoxy, branched ($C_3$-$C_6$) alkyl, phenyl, substituted phenyl, phenoxy, substituted phenoxy, phenylthio, or substituted phenylthio, and the rest of $R^{10}$ to $R^{14}$ are H.

32. A compound of claim 31 which is 8-fluoro-N-[2-(2-naphthyl)ethyl]-4-quinazolinamine.

33. A compound of claim 31 which is N-[2-(3-phenoxyphenyl)ethyl]-4-quinazolinamine.

34. A compound of claim 31 which is N-[2-(2-naphthyl)ethyl]-4-quinazolinamine.

35. A compound of claim 31 wherein one of $R^{10}$ to $R^{14}$ is $CF_3$.

36. The compound of claim 35 which is N-[2-[2-(trifluoromethyl)phenyl]ethyl]-4-quinazolinamine.

37. The compound of claim 35 which is N-[2-[3-(trifluoromethyl)phenyl]ethyl]-8-fluoro-4-quinazolinamine.

38. The compound of claim 35 which is N-[2-[4-(trifluoromethyl)phenyl]ethyl]-4-quinazolinamine.

39. A compound of claim 27 wherein Ar is a phenyl group of formula (2) wherein $R^{12}$ is other than H and $R^{10}$, $R^{11}$, $R^{13}$, and $R^{14}$ are H.

40. The compound of claim 31 which is 8-fluoro-N-[2-[4-(i-propyl)phenyl]ethyl]-4-quinazolinamine.

41. The compound of claim 31 which is 8-fluoro-N-[2-[4-(t-butyl)phenyl]ethyl]-4-quinazolinamine.

42. The compound of claim 31 which is 8-fluoro-N-[2-(4-phenoxyphenyl)ethyl]-4-quinazolinamine.

43. The compound of claim 31 which is 8-fluoro-N-(2-[1,1'-biphenyl]-4-ylethyl)-4-quinazolinamine.

44. The compound of claim 31 which is N-[2-(1,1'-biphenyl)-4-ylethyl]-4-quinazolinamine.

45. The compound of claim 31 which is N-(2-[1,1'-biphenyl]-4-ylethyl)-N-(4-quinazolinyl)acetamide.

46. A compound of claim 1 wherein Y is —$CR^8R^9$—W—Ar.

47. A compound of claim 46 wherein $R^8$ and $R^9$ are both H.

48. A compound of claim 46 wherein Z is H.

49. A compound of claim 46 wherein W is —$(CH_2)_2$—.

50. A compound of claim 46 wherein $R^4$ is F and the rest of $R^1$ to $R^4$ are H.

51. A compound of claim 46 wherein Ar is naphthyl, or a phenyl group of formula (2) wherein one of $R^{10}$ to $R^{14}$ is Cl, Br, ($C_1$-$C_{10}$) alkyl, halo ($C_1$-$C_4$) alkyl, ($C_1$-$C_4$) alkoxy, ($C_1C_4$) alkylthio, halo ($C_1$-$C_4$) alkoxy, branched ($C_3$-$C_6$) alkyl, phenyl, substituted phenyl, phenoxy, substituted phenoxy, phenylthio, or substituted phenylthio, and the rest of $R^{10}$ to $R^{14}$ are H.

52. A compound of claim 51 wherein Ar is a phenyl group of formula (2) wherein $R^{12}$ is other than H and $R^{10}$, $R^{11}$, $R^{13}$, and $R^{14}$ are H.

53. A fungicidal combination comprising at least 1% of a compound of claim 1 in combination with a second plant fungicide.

54. A fungicidal composition comprising a disease inhibiting and phytologically acceptable amount of a compound of claim 1 in combination with a phytologically acceptable carrier.

55. A fungicidal method which comprises applying to the locus of a plant pathogen a disease inhibiting and phytologically acceptable amount of a compound of claim 1.

56. A method of inhibiting an insect or mite which comprises applying to a locus of the insect or mite an insect- or mite-inactivating amount of a compound of claim 1.

57. The method of claim 56 wherein the compound of claim 1 is one in which
Y is X—W—Ar;
Z is H; and
Ar is a substituted phenyl group of formula (2) wherein $R^{12}$ is Cl, Br, ($C_1$-$C_4$) alkyl, branched ($C_3$-$C_4$) alkyl, phenyl, substituted phenyl, phenoxy, substituted phenoxy, phenylthio, or substituted phenylthio, and the rest of $R^{10}$ to $R^{14}$ are H.

58. The method of claim 56 in which the compound of claim 1 is 4-[2-[4-(t-butyl)phenyl]ethoxy]quinazoline.

59. An insecticide or miticide composition comprising an insect- or mite-inactivating amount of a compound of claim 1 in combination with a phytologically acceptable carrier.

60. An insecticide or miticide combination comprising at least 1% by weight of a compound of claim 1 in combination with a second insecticide or miticide.

61. A method of inhibiting an insect or mite which comprises applying to the locus of the insect or mite an insect-inactivating or mite-inactivating amount of a combination of claim 60.

* * * * *